(12) United States Patent
Eckels et al.

(10) Patent No.: US 6,638,514 B1
(45) Date of Patent: Oct. 28, 2003

(54) MULTIVALENT DENGUE VIRUS VACCINE

(75) Inventors: Kenneth H. Eckels, Rockville, MD (US); Joseph R. Putnak, Silver Spring, MD (US); Doria R. Dubois, Wheaton, MD (US); Bruce L. Innis, Haverford, PA (US); Charles H. Hoke, Columbia, MD (US); Sun Wellington, Rockville, MD (US); Niranjan Kanessa-thasan, Rockville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/535,117

(22) Filed: Mar. 24, 2000

Related U.S. Application Data

(60) Provisional application No. 60/181,724, filed on Feb. 11, 2000, and provisional application No. 60/126,313, filed on Mar. 26, 1999.

(51) Int. Cl.$^7$ .............................................. A61K 39/193

(52) U.S. Cl. ................................. 424/218.1; 424/202.1

(58) Field of Search ........................... 424/186.1, 202.1, 424/218.1

(56) References Cited

PUBLICATIONS

Trent, D. W., et al., "Genetic variation and microevolution of dengue 2 virus in Southeast Asia.", Virology, (1989 Oct.) 172(2): 523–35.*
Rico–Hesse, R., et al., "Molecular evolution of dengue type 2 virus in Thailand.", American Journal of Tropical Medicine and Hygiene, (1998 Jan.) 58(1):96–101.*
Holmes, E. C. and S. S. Burch, "The causes and consequences of genetic variation in dengue virus.", Trends in Microbiology, (2000 Feb.) 8(2):74–7.*
Harrison, V. R., et al., "Virulence and immunogenicity of a temperature–sensitive dengue–2 virus in lower primates.", Infection and Immunity, (1977 Oct.) 18(1):151–6.*
Kinney, R. M., et al., "Construction of infectious cDNA clones for dengue 2 virus:strain 16681 and its attenuated vaccine derivative, strain PDK–53.", Virology, (Apr. 14, 1997) 230(2):300–8.*
PCT International Search Report from international application PCT/US00/08199 (corresponding to 09/535,117), dated Oct. 23, 2000 (9 pages).
Jirakanjanakit et al., "The use of Toxorhynchites splendens for identification and quantitation of serotypes contained in the tetravalent live attenuated dengue vaccine", Vaccine, GB Butterworth Scientific. Guildford, vol. 17, No. 6, Feb. 1999, pp. 597–601.
Hoke et al., "Preparation of an attenuated Dengue 4 virus vaccine II safety and immunogenicity in humans", American J. of Tropical Medicine & Hygiene, Lawrence, KS, US, vol. 43, No. 2, Aug. 1990, pp. 219–226.

D. J. Gubler, "The global pandemic of dengue/dengue haemorrhagic fever: Current status and prospects for the future", Annals Academy of Medicine Singapore, vol. 27, No. 2, Mar. 1998, pp. 227–234.
Putnak et al., "Development of a purified, inactivated, dengue–2 virus vaccine prototype in vero cells: immunogenicity and protection in mice and rhesus monkeys", J. of Infectious Diseases, vol. 174, No. 6, 1996, pp. 1176–1184.
Puri Beena et al., "Molecular analysis of dengue virus attenuation after serial passage in primary dog kidney cells", J. of General Virology, vol. 78, No. 9, 1997, pp. 2287–2291.
Marchette et al., "Preparation of an attenuated dengue 4 virus vaccine I pre–clinical studies", American J. of Tropical medicine & Hygiene, Lawrence, KS, US, vol. 43, No. 2, Aug. 1990, pp. 212–218.
Bhamarapravati et al., "Live attenuated tetravalent dengue vaccine", Vaccine, GB Butterworth Scientific Guildford, vol. 18, Mar. 2000, pp. 44–47.
Botstein and Shortle, 1985, "Strategies and applications of in vitro mutagenesis", Science, vol. 229, No. 4719, pp. 1193–1201.
Clarke and Casals, 1958, "Techniques for hemagglutination and hemagglutination–inhibition with arthropod–borne viruses", Am. J. Trop. Med. Hyg., 7, 561–573.
Halstead et al., 1984, "Selection of attenuated Dengue 4 viruses by serial passage in primary kidney cells," Am J. Trop. Med. Hyg, 33(4), pp. 654–665, 666–671, 672–678, 679–683.
Hayflick, 1988, "History of cell substrates used for human biologicals", Symposium on Continuous Cell Lines as Substrates for Biologicals, Arlington, Virginia, USA, pp. 11–26.
Hoke et al., 1990, "Preparation of an attenuated Dengue 4 virus vaccine", Am J. Top. Med. Hyg., 43(2), pp. 219–226.
Marchette, 1990, "Preparation of an attenuated Dengue 4 virus vaccine", Am J. Top. Med. Hyg., 43(2), pp. 212–218.
Mizrahi, ed., Viral Vaccines, "WHO Attitude to Viral Vaccines", Wiley–Liss, New York (1990), pp. 39–60.
Putnak et al, 1996, "Development of a purified inactivated, Dengue–2 virus vaccine prototype in vero cells: immunogenecity and protection in mice nad Rhesus monkeys," J. Infectious Dis., 174, pp.1176–1184.
Russell, et al., "A plaque reduction test for dengue virus neutralizing antibodies", J. Immunology, vol. 99, No. 2, 1967, pp.285–290.
Scott, 1983, "Dengue 2 vaccine: Dose response in volunteers in relation to yellow fever immune status," J. Infectious Diseases, vol., 148, No. 6, pp.1055–1060.

(List continued on next page.)

Primary Examiner—Laurie Scheiner
Assistant Examiner—J. S. Parkin
(74) Attorney, Agent, or Firm—Elizabeth Arwine

(57) ABSTRACT

The present invention provides vaccine compositions of attenuated dengue virus. More specifically, the attenuated virus is produced by serial passage in PDK cells. The invention also provides methods for stimulating the immune system of an individual to induce protection against all four dengue virus serotypes by administration of attenuated dengue-1, dengue-2, dengue-3, and dengue-4 virus.

12 Claims, 11 Drawing Sheets

OTHER PUBLICATIONS

Sukhavachana et al, 1966, "Tissue culture techniques for the study of dengue viruses", Abreges des Communications, Bull. WHO 35, pp. 65–66.

Deller and Smith, 1984, Laboratory Methods, "Oligonucleotide–directed mutagenesis: a simple method using two oligonucleotide primers and a single–stranded DNA template", DNA, vol. 3, No. 6, pp.479–488.

Bhamarapravati, 1987, "Immunization with a live attenuated dengue–2–virus candidate vaccine: clinical, immunological and biological responses in adult volunteers", Bull. WHO, 65(2), pp.189–195.

Conrad et al., "Infection with *Nippostrongylus Brasiliensis* or injection of anti–IgD antibodies markedly enhances Fc–receptor–mediated interleukin 4 production by non–B, non–T cells", J. Exp. Med., vol. 171, pp.1497–1508.

Dharakul, et al., "Dengue virus–specific memory T cell responses in human volunteers receiving a live attenuated dengue virus Type 2 candidate vaccine", J. Infect. Dis., vol. 170, pp. 27–33.

Edelman et al., "A live attenuated Dengue–1 vaccine candidate passaged in primary dog kidney cell culture is attenuated and immunogenic for humans", 1994, Am. J. Trop. Med. Hyg., 170, pp. 1448–1455.

Halstead, 1978, "Studies on the attenuation of Dengue 4", Asian J. Infectious Dis., vol. 2, pp. 112–117.

Halstead, 1970, "Long 'cure' improves results of pig heterograft heart valves", JAMA, vol. 211, No. 6, pp. 911–916.

Johnson and Roehrig, "New mouse model for Dengue virus vaccien testing", J. Virology, Jan. 1999, vol. 73, No. 1, pp. 783–786.

Kontny et al., "Gamma interferon augments Fcγ receptor–mediated Dengue virus infection of human monocytic cells", J. Virology, Nov. 1988, vol. 62, No. 11, pp. 3928–3933.

Kurane et al., "Dengue virus–specific human T cell clones", J. Exp. Med., vol. 170, 1989, pp. 763–775.

Kurane et al., "Activation of T lymphocytes in dengue virus infections", J. Clin. Invest., vol. 88, 1991, pp. 1473–1480.

Kurane et al., "T cell activation in vivo by Dengue virus infection", J. Clin. Lab. Immunol., 1995, vol. 46, pp.35–40.

Peters, "Actions of cytokines on the immune response and viral interactions: an overview", Hepatology, vol. 23, 1996, pp. 909–916.

Sittisombut et al., "Lack of augmenting effect of interferon–γ on Dengue virus multiplication in human peripheral blood monocytes", J. Medical Virology 45:43–49, 1995.

Sabin, 1959, "Dengue", Viral and Rickettsial Infections of Man, Philadelphia: JB Lippincott Company, pp. 361–373.

Simmons et al., "Experimental Studies of Dengue", 1931, Manila BUreau of Printing, pp. 1–489.

Wisseman and Sweet, "Immunological studies with Group B arthropod–borne viruses", Am. J. Trop. Med. Hyg., vol. 11, pp. 570–575 (1962).

Yuill et al., "Dengue–virus recovery by direct and delayed plaques in LLC–MK2 cells", Am. J. Trop. Med. Hyg., Vol 17, 1968, pp. 441–448.

Edelman, et al., "A Live Attenuated Dengue–1 Vaccine Candidate (45AZ5) Passaged in Primary Dog Kidney Cell Culture SIs Attenuated and Immunogenic for Humans", J. Infectious Diseases, 1994:170:1448–1455 (Dec.).

Angsubharkorn et al., "Dengue–3 (16562) PGMK 33 Vaccine: Neurovirulence, Viremia and Immune Responses in *Macaca Fascicularis*", Southeast Asian J. Trop. Med. Public Health, vol. 25, No. 3, Sep. 1994.

(XP–002150293) Sun et al., Program Abstracts from the First Annual Conference on Vaccine Research, May 30–Jun. 1, 1998, "Phase I Study of Two Doses of Monovalent Live–Attenuated Dengue Virus Vaccines" (2 pages).

Vaughn, et al., "Testing of a dengue 2 live–attenuated vaccine (strain 16681 PDK 53) in ten American volunteers", Vaccine, vol. 14, No. 4, pp. 329–336, 1996.

Smith and Wright, "Synthesis of Proteins and Glycoproteins in Dengue Type 2 Virus–Infected Vero and *Aedes albopictus* Cells", J. Gen. Virol., (1985) 66: 559–571.

Kraiselburd, E., "Comparative Infectivity Determination of Candidate Live Dengue Virus Vaccine in Monkeys, Mosquitoes and cell cultures", Annual and Final Report, May 1987, pp. 1–20.

Osatomi, K., "Complete Nucleotide Sequence of Dengue Type 3 Virus Genome RNA", Virology 176:643–647 (1990).

Puri, B., "Molecular analysis of dengue virus attenuation after serial passage in primary dog kidney cells", J. General Virology (1997) 78:2287–2291.

\* cited by examiner

FIG.3

| Formulation DEN1-2-3-4 | No. Subjects | Mean Reactogenicity Index | | | No. viremic (cell culture) | Neutralizing Antibody to ≥ 3 serotypes |
|---|---|---|---|---|---|---|
| | | 1st dose | 2nd dose | 3rd dose | | |
| LLLL | 3 | 5 | 1 | ND | 1/3 | 2/3 |
| HLLL | 4 | 32 | 4 | ND | 3/4 | 4/4 |
| LHLL | 3 | 2 | 1 | ND | 3/3 | 0/3 |
| LLLH | 3 | 3 | 2 | ND | 1/3 | 0/3 |
| LLHL | 4 | 11 | 0 | ND | 4/4 | 1/4 |
| LHLH | 3 | 4 | 2 | ND | 1/3 | 0/3 |
| HLHL | 4 | 20 | 1 | ND | 4/4 | 2/4 |
| LHHL | 4 | 2 | 2 | ND | 0/4 | 1/4 |
| LLHH | 4 | 8 | 7 | ND | 2/4 | 1/4 |
| HLLH | 4 | 11 | 0 | ND | 2/4 | 4/4 |
| HHLL | 3 | 14 | 1 | ND | 3/3 | 3/3 |
| LHHH | 4 | 4 | 5 | ND | 0/4 | 1/4 |
| HLHH | 4 | 8 | 2 | ND | 1/4 | 3/4 |
| HHLH | 4 | 2 | 3 | ND | 1/4 | 4/4 |
| HHHL | 3 | 2 | 2 | ND | 0/3 | 2/3 |
| HHHH | 10 | 9 | 3 | 0 | 4/10 | 6/10 |
| Total (mean) | 64 | (9) | (2) | (0) | 47% | 53% |

\* 5 subjects received dose at 4 months, 4 of these 5 seroconverted to ≥ 3 serotypes.
H = undiluted reconstituted vaccine, L = 1.5 log dilution of H.

FIG. 4

| Volunteer | Vaccine | Schedule | Serotypes Neutralizing Ab Seroconversion 30 days after: | | |
|---|---|---|---|---|---|
| | | | Dose 1 | Dose 2 | Dose 3 |
| 33 | Full-dose Tetraval. | 0,1 | 1,2,3,4 | 1,2,3,4 | ND |
| 34 | Full-dose Tetraval. | 0,1 | 2 | 1,2 | ND |
| 35 | Full-dose Tetraval. | 0,1 | 1,2,3,4 | 1,2,3,4 | ND |
| 36 | Full-dose Tetraval. | 0,1 | 1 | 1,3 | ND |
| 37 | Full-dose Tetraval. | 0,1,4 | 1 | 1 | 1,2,3 |
| 38 | Full-dose Tetraval. | 0,4 | 1,2 | 1,2,3 | ND |
| 39 | Full-dose Tetraval. | 0,1,4 | 1,3,4 | 1,3 | 1,2,3,4 |
| 40 | Full-dose Tetraval. | 0,1,4 | 1 | 1 | 1,3 |
| 41 | Full-dose Tetraval. | 0,1,4 | 2 | 2 | 1,2,3,4 |
| 42 | Full-dose Tetraval. | 0,1 | 2 | 1,2 | ND |

FIG. 5

| Formulation DEN1-2-3-4 | Volunteer No. | Reactogenicity Index 1st dose | Reactogenicity Index 2nd dose (1m) | Viremia[1] 1st dose | Viremia[1] 2nd dose | Serotypes Neutralizing Antibody 30 days after: 1st dose | Serotypes Neutralizing Antibody 30 days after: 2nd dose |
|---|---|---|---|---|---|---|---|
| HLLL | 02-1 | 31 | 0 | + | - | 1,2,3,4 | 1,2,3,4 |
| HLLL | 02-2 | 23 | 0 | - | - | 1,2,3,4 | 1,3 |
| HLLL | 02-3 | 55 | 0 | + | - | 1,3,4 | 1,3 |
| HLLL | 02-4 | 18 | 0 | + | + | 1,2,3 | 1 |
| HLLH | 10-1 | 3 | 0 | + | - | 1,3 | 1,2,3,4 |
| HLLH | 10-2 | 0 | 0 | - | - | 1 | 1,2,3 |
| HLLH | 10-3 | 37 | 1 | - | - | 1,2,3 | 1,2,3 |
| HLLH | 10-4 | 5 | 0 | + | - | 1,2,3 | 1,3 |
| HHLL | 11-1 | 8 | 0 | + | + | 1,2,3 | 1 |
| HHLL | 11-2 | 20 | 2 | + | - | 1,2 | 1,2,3 |
| HHLL | 11-3 | 15 | 0 | + | - | 1,2,3 | 1,2 |
| HLHH | 13-1 | 6 | 4 | - | - | 1 | 1,4 |
| HLHH | 13-2 | 0 | 0 | - | - | 1,3,4 | 1,3,4 |
| HLHH | 13-3 | 4 | 0 | - | - | 1,2,*,4 | 1,2,*,4 |
| HLHH | 13-4 | 21 | 2 | + | - | 1,2,3,4 | 1,2,3,4 |
| HHLH | 14-1 | 0 | 0 | - | - | 1,2 | 1,2,3 |
| HHLH | 14-2 | 9 | 0 | + | - | 1,2,4 | 1,2,3,4 |
| HHLH | 14-3 | 0 | 2 | - | - | None | 1,2,3,4 |
| HHLH | 14-4 | 0 | 0 | - | - | None | 1,3,4 |
| Mean | | 13.4 | 0.6 | | | | |

[1] by delayed plaque method on C6/36 and Vero.
* result pending

Granzyme B gel band intensity*

| ID | Control | CD8dep | CD3dep | Unstim | Control | CD4dep |
|---|---|---|---|---|---|---|
| 3 | +++- | ++++ | +--- | ±--- | ++-- | ++-- |
| 4 | ++++ | ++++ | ++++ | | | |
| 10 | ++++ | ++++ | +++- | | | |
| 11 | ++++ | ++++ | ±--- | | | |
| 12* | ++++ | ++++ | ±--- | | | |
| 13 | ++++ | ++++ | +++- | | ++++ | ++++ |
| 15 | ++++ | ++++ | +++- | | ++++ | ++++ |
| 16 | +++- | ++-- | +--- | ---- | ++++ | ++++ |
| 17 | ++++ | ++++ | +--- | ---- | ++++ | ++++ |
| 20 | ++-- | ++-- | ++-- | | | |
| 22 | +++- | ++-- | +--- | ±--- | | |
| 29 | ++++ | ++++ | ±--- | | ++++ | ++++ |
| 31 | ++++ | ++++ | +--- | +--- | ++++ | ++++ |
| 33T | +++- | +--- | ---- | | | |
| 35T* | ++++ | ++++ | ±--- | ±--- | | |
| 36T | ++++ | ++++ | ±--- | ±--- | | |

MULTIVALENT DENGUE VIRUS VACCINE

This application claims the benefit of priority under 35 U.S.C. §119(e) from U.S. application Ser. No. 60/126,313 filed on Mar. 26, 1999, still pending, and U.S. application Ser. No. 60/181,724 filed on Feb. 11, 2000, still pending.

INTRODUCTION

Dengue fever is caused by any of four serotypes of dengue virus, dengue-1, dengue-2, dengue-3, and dengue-4, which are transmitted to humans by mosquitoes. In adults, dengue infections typically cause self-limited but incapacitating acute illness with fever, muscle pains, headache and an occasional rash. The illness may be complicated by hemorrhagic fever, which may be manifested by a positive tourniquet test, spontaneous petechiae, frank bleeding, and/or shock. Dengue-hemorrhagic fever is fatal in about 0.5% of cases. Patients who have antibody from an earlier dengue infection who are subsequently infected by another dengue strain have been shown to be at higher risk for dengue hemorrhagic fever.

The mosquito vectors of dengue viruses are found in all tropical and sub-tropical areas of the world and in some temperate areas of the United States, Europe, Africa, and the Middle East. In recent years, endemic and epidemic dengue infections have occured in Central and South Ameria, Southeast Asia, India, Africa, the Caribbean and Pacific regions. Vector control is impractical.

An effective vaccine is needed which should confer protection against all four serotypes of dengue.

SUMMARY OF THE INVENTION

The present invention satisfies the need discussed above. The present invention relates to vaccine compositions comprising attenuated dengue virus from all four serotypes. The attenuated virus is provided in an amount sufficient to induce an immune response in a human host, in conjuction with a physiologically acceptable vehicle and may optionally include an adjuvant to enhance the immune response of the host.

Therefore, it is one object of the present invention to provide an attenuated dengue virus composition comprising attenuated more than one dengue virus selected from the group consisting of dengue-1, dengue-2, dengue-3, and dengue-4, in any combination.

It is another object of the present invention to provide methods for stimulating the immune system of an individual to induce protection against dengue virus. These methods comprise administering to the individual an immunologically sufficient amount of dengue virus from all four serotypes which have been attenuated by serial passage.

BRIEF DESCRIPTION OF THE DRAWINGS

FIG. 3: Table showing results of dose-ranging tetravalent dengue vaccine studies.

FIG. 4: Table showing Immunogenicity of full-dose tetravalent dengue vaccine in 10 subjects.

FIG. 5: Table showing details of selected formulations of tetravalent vaccine studies.

DETAILED DESCRIPTION

Figure 1:
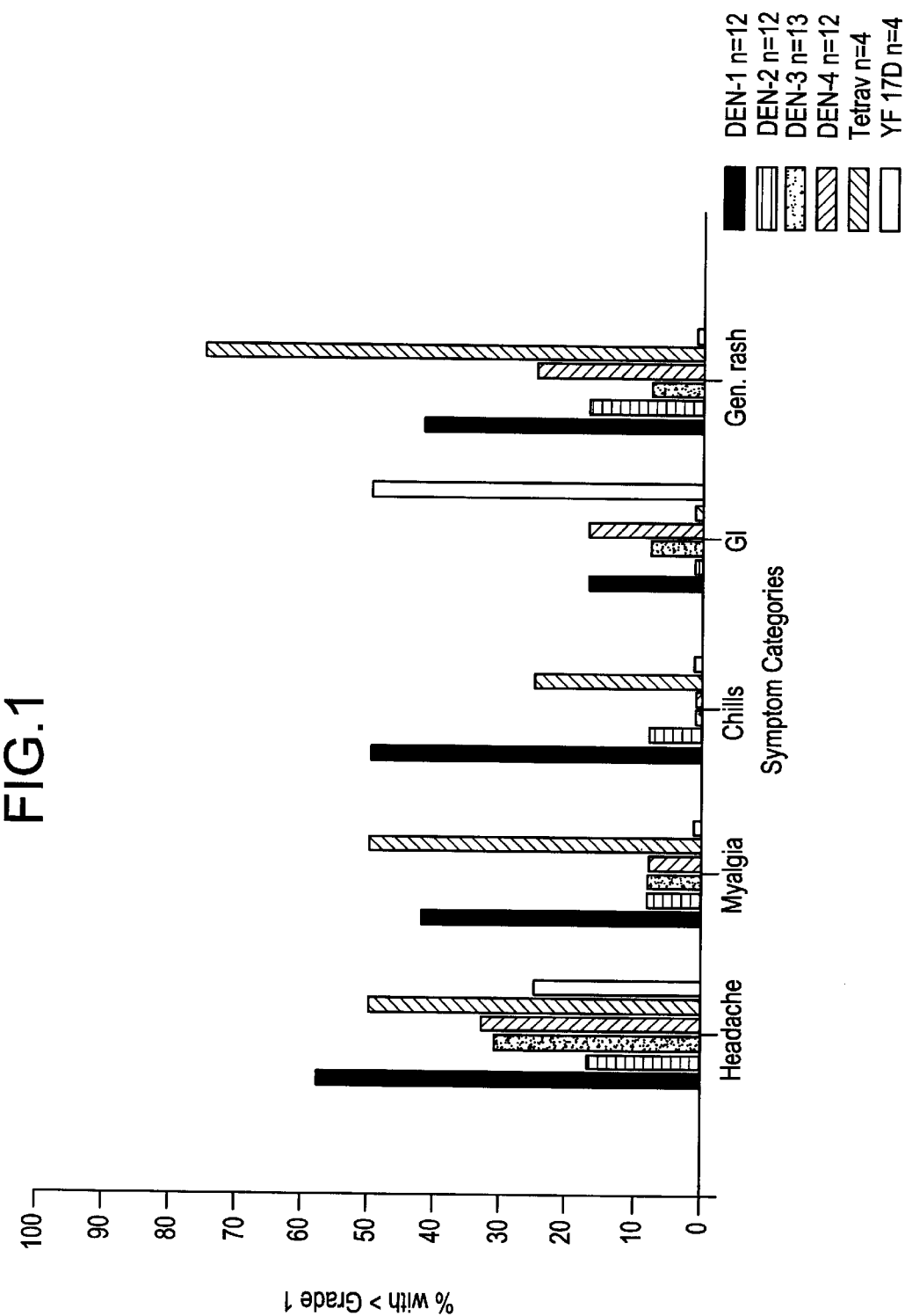
FIG. 1: Occurrence of >Grade 1 symptoms as a result of vaccine administration.

The present invention provides attenuated dengue virus of all four serotypes suitable for vaccine use in humans. The dengue viruses described herein were produced by serial passaging of an infectious dengue virus isolate in a suitable host cell line such as primary dog kidney cells so that mutations accumulate that confer attenuation on the isolate. Serial passaging refers to the infection of a cell line with a virus isolate, the recovery of the viral progeny from the host cells, and the subsequent infection of host cells with the viral progeny to generate the next passage.

Preferably, the following attenuated viruses are used in the compositions of the present invention even though other viris compositions, of any of the serotypes, whether attenuated or inactivated, can be used in combination with the attenuated strains described in the present invention. The attenuated dengue-1 virus, derived from 45AZ5 isolate, PDK 20, was deposited on Apr. 30, 1999 under the terms of the Budapest Treaty with the American Type Culture Collection (ATCC) of 10801 University Boulevard, Manassas, Va. 20110-2209, U.S.A., and granted the accession number of VR-2648. The attenuated dengue-1 virus, derived from 45AZ5 isolate, PDK 27, was deposited on Nov. 21, 2002 under the terms of the Budapest Treaty with the American Type Culture Collection (ATCC) of 10801 University Boulevard, Manassas, Va. 20110-2209, U.S.A., and granted the accession number of PT-A4810.

The attenuated dengue-2 derived from S16803 isolate, was deposited on Apr. 30, 1999 under the terms of the Budapest Treaty with the American Type Culture Collection (ATCC) of 10801 University Boulevard, Manassas, Va. 20110-2209, U.S.A., and granted the accession number of VR-2653.

The attenuated dengue-3 derived from CH53489 isolate, was deposited on Apr. 30, 1999 under the terms of the Budapest Treaty with the American Type Culture Collection (ATCC) of 10801 University Boulevard, Manassas, Va. 20110-2209, U.S.A., and granted the accession number of VR-2647.

The attenuated dengue4 derived from the 341750 isolate, PDK 20, was deposited on Apr. 30, 1999 under the teris of the Budapest Treaty with the American Type Culture Collection (ATCC) of 10801 University Boulevard, Manassas, Va. 20110-2209, U.S.A., and granted the accession number of VR-2652. The attenuated dengue-4 virus, derived from 341750 isolate, PDK 6, was deposited on Nov. 21, 2002 under the terms of the Budapest Treaty with the American Type Culture Collection (ATCC) of 10801 University Boulevard, Manassas, Va. 20110-2209, U.S.A., and granted the accession number of PTA4811.

The attenuated dengue-4 virus derived from the 341750 isolate, deposited under the terms of the Budapest Treaty with the American Type Culture Collection (ATCC) of 10801 University Boulevard, Manassas, Va. 20110-2209, U.S.A., and granted the accession number of VR-2652.

Serial passaging of a virulent (disease-causing) strain of dengue results in the isolation of modified virus which may be attenuated, i.e., infectious, yet not capable of causing disease. These modified viruses are tested in monkeys for reduced infectivity. Those that have reduced infectivity are subsequently tested in humans. Humans are the only primate that will exhibit signs of clinical disease. The viruses that show minimal to no clinical reactivity but still infect and induce an immune response are attenuated.

In one embodiment of the invention, a virulent dengue isolate from all four dengue serotypes was serially passaged in primary dog kidney (PDK) cells to derive the attenuated strains. Serial passaging was performed by infecting PDK cells with the virulent strain, incubating the infected cells for several days, and collecting the supernatant culture fluids containing virus. The harvested virus was then applied to fresh PDK cells to generate the next passage.

Various passages in the series were tested for clinical effect after final passage in fetal Rhesus monkey lung cells (FRhL). FRhL cells were used to optimize virus titers wherein, in general, passage 1 was considered the master seed, passage 2 was considered the production seed, and passage 3 was considered the vaccine lot. Vaccines were prepared at various PDK passage levels, and the vaccine products tested for attenuation in monkeys and humans. The virulence of a passaged virus, i.e., the ability to cause disease, was assessed by daily monitoring of symptoms such as temperature (fever), headache, rash, to name a few. The passage was considered attenuated, as judged by the inability of this virus to elicit clinical signs of dengue disease in vaccinees.

Propagation of the attenuated viruses of the invention may be in a number of cell lines which allow for dengue virus growth. Dengue virus grows in a variety of human and animal cells. Preferred cell lines for propagation of attenuated dengue viruses for vaccine use include DBS-FRhL-2, Vero cells and other monkey cells. Highest virus yields are usually achieved with heteroploid cell lines such as Vero cells. Cells are typically inoculated at a multiplicity of infection ranging from about 0.01 to 0.005, and are cultivated under conditions permissive for replication of the virus, e.g., at about 30–37° C. and for about 3–5 days, or as long as necessary for virus to reach an adequate titer. Virus is removed from cell culture and separated from cellular components, typically by well known clarification procedures, e.g., centrifugation, and may be further purified as desired using procedures well known to those skilled in the art.

The isolation of an attenuated virus may be followed by a sequence analysis of its genome to determine the basis for the attenuated phenotype. This is accomplished by sequencing the viral DNA and identifying nucleotide changes in the attenuated isolate relative to the genomic sequence of a control virus. Therefore, the molecular changes that confer attenuation on a virulent strain can be characterized.

One embodiment of the invention provided herein, includes the introduction of sequence changes at any of the positions listed in the table above, alone or in combination, in order to generate attenuated virus progeny. Viral genomes with such alterations can be produced by any standard recombinant DNA techniques known to those skilled in the art (Ausubel et al., *Current Protocols in Molecular Biology*, Greene Publishing Associates & Wiley Interscience, New York, 1989) for introduction of nucleotide changes into cloned DNA. A genome may then be ligated into an appropriate vector for transfection into host cells for the production of viral progeny.

The ability to generate viral progeny through plasmid-mediated introduction of a viral genome can also be used to produce viruses with defined molecular changes. In this embodiment of the invention, stable virus stocks can be produced that contain altered sequences that confer desired properties on the virus, for example, reduced virulence. This approach can also be used to assess the effect of molecular changes on various properties of the virus, i.e. antigenic type, virulence, or attenuation by introducing desired sequence changes into the viral genome, producing virus progeny from the genome, and recovering the virus progeny for characterization. In addition, this approach can be used to construct a virus with heterologous sequences inserted into the viral genome that are concurrently delivered by the virus to generate an immune response against other diseases.

Construction of viral genomes with defined molecular changes can be accomplished using standard techniques such as oligonucleotide-directed, linker-scanning or polymerase chain reaction-based mutagenesis techniques known to those skilled in the art (Zoller and Smith, 1984, *DNA* 3,479–488; Botstein and Shortle, 1985, *Science* 229, 1193). Ligation of the genome into a suitable vector for transfer may be accomplished through standard techniques known to those skilled in the art. Transfection of the vector into host cells for the production of viral progeny may be done using any of the standard techniques such as calcium-phosphate or DEAE-dextran mediated transfection, electroporation, protoplast fusion, and other techniques known to those skilled in the art (Sambrook et al., *Molecular Cloning: A laboratory Manual*, Cold Spring Harbor Laboratory Press, 1989).

For vaccine use, the attenuated viruses of the invention can be used directly in vaccine formulations, or lyophilized, preferably in a stabilizer (Hoke, 1990, Am J Trop Med Hyg 43, 219–226), as desired, using lyophilization protocols well known to the artisan. Lyophilized virus will typically be maintained at about 4° C. When ready for use, the lyophilized virus is reconstituted in water, or if necessary, in a stabilizing solution, e.g., saline or comprising $Mg^{++}$ and HEPES, with or without adjuvant, as further described below. All references cited herein are hereby incorporated in their entirety by reference thereto.

Thus, dengue virus vaccines of the invention contain as an active ingredient an immunogenically effective amount of more than one attenuated dengue virus chosen from the group consisting of dengue-1, dengue-2, dengue-3, and dengue-4 as described herein. The attenuated virus composition may be introduced into a subject, particularly humans, with a physiologically acceptable vehicle and/or adjuvant. Useful vehicles are well known in the art, and include, e.g., water, buffered water, 0.4% saline, 0.3% glycine, hyaluronic acid and the like. The resulting aqueous solutions may be packaged for use as is, or lyophilized, the lyophilized preparation being rehydrated prior to administration, as mentioned above. The compositions may contain pharmaceutically accepatable auxilliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

Administration of the live attenuated viruses disclosed herein may be carried out by any suitable means, including both parenteral injection (such as intraperitoneal, subcutaneous, or intramuscular injection), by in ovo injection in birds, orally and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the virus as an aerosol suspension, and then causing the subject to inhale the respirable particles. Methods and apparatus for administering respirable particles of pharmaceutical formulations are well known, and any conventional technique can be employed. As a result of the vaccination the host becomes at least partially or completely immune to dengue virus infection of the serotypes administered, or resistant to developing moderate or severe dengue viral infection.

The vaccine composition containing the attenuated dengue viruses of the invention are administered to a person susceptible to or otherwise at risk of dengue virus infection to enhance the individual's own immune response capabilities. Such an amount is defined to be a "immunogenically effective dose". In this use, the precise amount again depends on the subject's state of health and weight, the mode of administration, the nature of the formulation, etc., but generally range from about $10^2$ to $10^6$ pfu of each serotype of dengue virus per subject. The amount of virus vaccine of each serotype may be adjusted, i.e. increased or decreased, to result in a formulation which provides sufficient protection from infection with the desired dengue virus. When the four serotypes are combined, a preferred composition comprises equal amount of each dengue serotype. In any event, the vaccine formulations should provide a quantity of attenuated dengue virus of each of the serotypes sufficient to effectively protect the patient against serious or life-threatening dengue virus infection of a serotype in the vaccine formulation, and possibly other serotypes if crossprotection occurs.

The attenuated dengue viruses of the invention of one particular serotype can be combined with attenuated viruses of other serotypes of dengue virus to achieve protection against multiple dengue viruses. Typically the different modified viruses will be in admixture and administered simultaneously, but may also be administered separately.

In some instances it may be desirable to combine the attenuated dengue virus vaccines of the invention with vaccines which induce protective responses to other agents.

Single or multiple administration of the vaccine compositions of the invention can be carried out. Multiple administration may be required to elicit sufficient levels of immunity. Levels of induced immunity can be monitored by measuring amount of neutralizing secretory and serum antibodies, and dosages adjusted or vaccinations repeated as necessary to maintain desired levels of protection.

The following examples are provided by way of illustration, not limitation.

The following MATERIALS AND METHODS were used in the examples that follow.

Materials and Methods for Vaccine Production.

Virus strains. DEN viruses were passaged in primary dog kidney (PDK) cell cultures following isolation from human and mosquito sources. Table 1 lists the strains that were adapted and passaged in PDK cells. After passage in PDK cells, virus strains were further adapted to FRhL cells for seed and vaccine production. This consisted of an additional 3–4 passages for final vaccine lot preparation. Parental virus strains, also listed in Table 1, were derived from low, cell culture passages in cells that were permissive for DEN virus replication.

Vaccine production. DEN vaccines for all four serotypes were prepared in FRhL cell culture using a similar procedure. FRhl cells, banked and pre-tested (see Table 2 for testing results) were removed from liquid nitrogen storage and plated in 150 $cm^2$ flasks in Eagle's minimum essential media (EMEM) (Biowhittaker, Waldersville, Md.) cell medium supplemented with non-essential amino acids, fetal bovine serum, FBS (2%) (Biowhittaker, Waldersville, Md.), and antibiotics. After the flasks reached confluency, medium was removed and flasks inoculated with DEN production seed diluted for an input of 0.01 MOI, and allowed to adsorb at 32° C. for 1 hr. Following adsorption-and feeding with fresh EMEM medium, flasks were returned to 32° C. for 4 days. On day 4 post-inoculation, medium from all flasks was discarded and cell monolayers were washed 3 times with 100 ml of Hanks BSS (Biowhittaker, Waldersville, Md.). After washing, flasks were fed with EMEM medium containing 0.25% human serum albumin (HSA, Alpha Therapeutic Corp, Los Angeles, Calif.) replacing FBS. After an additional two days of incubation at 32° C., supernatant culture fluids were removed from all flasks and pooled. After sampling for safety tests, the remaining culture fluids were pooled and clarified by filtration through a 0.45 micron, non-protein binding membrane filter. The filtered fluids were pooled and mixed with an equal volume of stabilizer containing 15% lactose and 5% HSA. The bulk, stabilized fluids were stored at −70° C. until freeze-dried. For final vialing, bulk, stabilized fluids were thawed rapidly at 41° C. and aliquoted in 3 ml volumes in serum vials. Trays of vials were frozen to a temperature of −40° C. in a Hull freeze-dryer, followed by drying for 1 day. Following capping, vials were stored at −20° C. in a monitored freezer.

Vaccine testing. All cell banks used for virus preparations as well as seed and vaccine lots were tested for the presence of contaminating agents. The test articles and results are listed in Table 2. No detectable contaminants were found in any of the products.

Rhesus monkey inoculation. Adult, male and female rhesus monkeys (6–15 kg) were immunized with the DEN vaccine lots or parent viruses by subcutaneous inoculation of 0.5 ml in the upper arm. Blood for virus isolation and antibody tests was drawn from the femoral vein prior to inoculation and every day for 14 days following inoculation. Blood was also drawn at 30 and 60 days following immunization. Virus challenges were performed similarly.

Virus isolation by amplification in C6/36 cells. Virus isolation by C6/36 cell culture amplification has been described in Putnak et al, 1996 (J. Infect Dis 174, 1176–1184). Briefly, following inoculation of monkeys, daily blood specimens were obtained from days 1 to 14. Serum was separated and frozen at −80° C. For recovery of virus from sera, thawed sera were diluted 1:3 in cell culture medium and used to inoculate 25 cm² flasks containing monolayers of C6/36 mosquito cells. Following adsorption of virus, flasks were maintained at 28° C. in EMEM maintenance medium. After 7 days, medium was changed and flasks incubated an additional 7 days. On day 14 post inoculation, supernatant culture fluids were decanted and frozen at −80° C. after mixing with an equal volume of heat inactivated fetal bovine serum (FBS). Frozen specimens were later assayed for infectious virus by plaque assay.

TABLE 1

Dengue virus strains used for development of live-attenuated vaccines.

| Serotype | Original Isolate | Vaccine strain: passage from human isolate | PDK passages selected for vaccine prep | FRhL passages for seed and vaccine prep | Parental strain: passage from human isolate |
|---|---|---|---|---|---|
| DEN-1 (West Pac 74; 45AZ5) | Human isolate, Nauru, 1974 | 20 × FRhL (with plaque selection and mutagenization with 5AZ); vaccine prep'd at p-20 caused dengue fever in 2 V015 | 10, 20, 27 | 1: master seed 2: production seed 3: vaccine lot | 9 × FRhL |
| DEN-2 (S16803) | Human isolate, Thailand, 1974 | 1 × mosquito; 4 × PGMK | 10, 20, 30, 40, 50 | 1: master seed 2: production seed 3: vaccine lot | 4 × PGMK; 2 × C6/36 |
| DEN-3 (CH53489) | Human isolate, Thailand, 1973 | 4 × PGMK; 5 × C6/36 | 10, 20, 30 | 1: master seed 2: production seed 3: vaccine lot | 4 × PGMK |
| DEN-4 (341750) | Human isolate, Columbia, 1982 | 1 × mosquito | 6, 10, 15, 20 | 1: pre-master seed (PDK-20 only) 2: master seed 3: production seed 4: vaccine lot | 1 × mosq; 5 × PGMK; 4 × FRhL |

TABLE 2

Pre-clinical testing of FRh1 cell banks and DEN LAV seeds and vaccine lots.

| Test | FRh1 cell banks | Master Seed | Production Seed | Vaccine (Bulk) | Vaccine (Final Container) |
|---|---|---|---|---|---|
| Sterility | x | x | x | x | x |
| Mycoplasma | x | | x | x | |
| RT | x | | x | | |
| Hemadsorption | x | | x | x | |
| Cell culture safety (4 cell lines) | x | | | x | |
| Embryonated egg safety | x | | | | |
| Animal safety: adult mice | x | | | x | |
| Animal safety: suckling mice | x | | | x | |
| Animal safety: guinea pigs | x | | | x | |
| Animal safety: rabbits | x | | | | |
| Tumorgenicity | x | NA | NA | NA | NA |
| Karyology | x | NA | NA | NA | NA |
| Monkey safety: neurovirulence | NA | | x (DEN-4) | | |
| Monkey infectivity/immunogenicity | NA | | x | | |
| Monkey efficacy | NA | | | | x (DEN-2, DEN-4) |
| Infectivity (plaque assay) | NA | x | x | x | x |
| General safety | NA | | | x | x |
| Residual moisture | NA | | | | x |
| Reconstituted pH | NA | | | | x |
| Reconstituted osmolality | NA | | | | x |

TABLE 2-continued

Pre-clinical testing of FRh1 cell banks and DEN LAV seeds and vaccine lots.

| Test | FRh1 cell banks | Master Seed | Production Seed | Vaccine (Bulk) | Vaccine (Final Container) |
|---|---|---|---|---|---|
| Endotoxin | NA | | | | x |
| Identity (DEN) | NA | x | x | | x |

TABLE 3

DEN virus strain sets adapted to PDK cells, used for inoculation of rhesus monkeys.

| DEN virus strain | Viruses | Inoc: PFU/0.5 ml | MKs viremic/ Total (Mean days viremia) | Mk seroconverted/ Total (GMT PRNT$_{50}$ at 1–2 mo post inoc) |
|---|---|---|---|---|
| DEN-1, 45AZ5 | PDK-0 (parent) | $3.3 \times 10^4$ | 4/4 (6.8) | 4/4 (760) |
| | PDK-10 (prod seed)* | $7.0 \times 10^4$ | 4/4 (4.75) | 4/4 (1030) |
| | PDK-20 (prod seed) | $1.7 \times 10^4$ | 4/4 (4.5) | 4/4 (640) |
| | PDK-27 (prod seed) | $1.8 \times 10^4$ | 0/4 (0) | 4/4 (50) |
| DEN-2, S16803 | PDK-0 (parent) | $5.0 \times 10^6$ | 4/4 (5) | 4/4 (600) |
| | PDK-10 (prod seed) | $3.8 \times 10^5$ | 4/4 (4.75) | 4/4 (570) |
| | PDK-20 (prod seed) | $2.2 \times 10^5$ | 4/4 (6.5) | 4/4 (920) |
| | PDK-30 (prod seed[1]) | $4.4 \times 10^5$ | 2/3 (3.3) | 4/4 (640) |
| | PDK-30 (prod seed[2]) | $2.1 \times 10^5$ | 3/3 (6.0) | 3/3 (640) |
| | PDK-40 (prod seed) | $1.0 \times 10^4$ | 2/4 (1) | 3/4 (90) |
| | PDK-50 (prod seed[1]) | $2.6 \times 10^6$ | 2/4 (1) | 4/4 (310) |
| | PDK-50 (prod seed[2]) | $5.9 \times 10^5$ | 3/4 (3.25) | 4/4 (280) |
| | PDK-50 (vaccine) | $1 \times 10^6$ | ND | 4/4 (270) |
| DEN-3, CH53489 | PDK-0 (parent) | $8.0 \times 10^3$ | 3/3 (3) | 3/3 (660) |
| | PDK-10 (prod seed) | $2.5 \times 10^{6@}$ | 2/3 (1.3) | 3/3 (150) |
| | PDK-20 (prod seed) | $1.0 \times 10^{6@}$ | 0/3 | 3/3 (130) |
| | PDK-30 (prod seed) | $9.3 \times 10^{5@}$ | 0/3 | 0/3 (<10) |
| DEN-4, 341750 | PDK-0 (parent) | $1.0 \times 10^3$ | 3/3 (4.7) | 3/3 (420) |
| | PDK-6 (prod seed) | $1.7 \times 10^5$ | 1/4 (0.5) | 4/4 (250) |
| | PDK-10 (prod seed) | $2.9 \times 10^5$ | 1/4 (1.3) | 2/4 (90) |
| | PDK-15 (prod seed) | $5.5 \times 10^4$ | 1/4 (0.25) | 2/4 (40) |
| | PDK-20 (prod seed) | $5.5 \times 10^4$ | 1/4 (0.25) | 2/4 (70) |
| | PDK-20 (vaccine) | $1.2 \times 10^5$ | 1/3 (0.3) | 3/3 (50) |

[1,2]Two separate monkey experimental groups.
@Plaque assay performed in C6/36 cells.

Plaque assays. Infectious virus was titrated from amplified viremia isolates or directly from monkey sera by plaque assay in Rhesus monkey kidney (LLC-Mk$_2$, ATCC CCL7) cells following the procedure of Sukhavachana et al. 1966 (Bull WHO 35, 65–66). Assays in C6/36 cells was performed as described in Putnak et al, 1996, supra.

Neutralization tests. DEN neutralizing antibodies were measured from monkey sera using a plaque reduction neutralization test similar to that used by Russell et al, 1967 (J Immunol 99, 285–290). Parent viruses listed in Table 1 were used to measure the plaque reduction 50% endpoint (PRNT50) in serum specimens.

EXAMPLE 1

DEN virus modification in PDK cells and vaccine lot production. DEN virus strains selected for vaccine development had a variety of passage histories prior to PDK passage. In the case of DEN-4 341750 there was just one mosquito passage before inoculation of PDK cell culture, while DEN-1 West Pac 74 strain had a history of twenty FRhL cell passages prior to PDK passage (Table 1). With the exception of DEN-3, all strains adapted after a small number of PDK passages. For DEN-3, additional efforts were required to increase viral input in early passages in order to adapt this strain to PDK cells. As a general case after adaptation to PDK cells, DEN virus titers were found to be in the $10^4$–$10^5$ PFU/ml range. Attempts to increase titers were not successfull and alternative cell substrates were sought for vaccine production. DBS-FRhL-2 (FRhL) cells were selected for this purpose for several reasons: 1) DEN viruses replicate to titers of ca $10^6$ PFU/ml allowing manufacture of DEN vaccines in these cells; 2) the cells have been used for the preparation of several DEN vaccines that have been tested in Phase I clinical trials without adverse reactions that may be related to the vaccine cell substrate; 3) FRhL cells are normal, rhesus monkey lung diploid cells that have no tumorigenic potential and are free of reverse transcriptase activity and contaminating agents; 4) since the cells are "normal" diploid cells there is no regulatory or other requirement to purify the vaccines; 5) FRhL cell banks can be established at cell generations usable for vaccine manufacture starting with available, low passage cells. PDK passage therefore provides an excellent model for those who wish to study the empirical process of selective attenuation. But, just as PDK serial passage exerts a cumulative selection process, the further passage in another cell substrate provides its own selective pressure. It is not known whether or not FRhL passage increases or decreases the virulence of virus for humans. The use of stable cell lines that must be fully characterized only one time is appealing. However, the published experience with FRhL cells suggests that these cells may reverse or destabilize biological properties acquired during serial passage in PDK (Halstead et al., 1984, Am J Trop Med Hyg 33, 654–665; Halstead et al., 1984, Am J Trop Med Hyg 33, 666–671; Halstead et al., 1984, Am J Trop Med Hyg 33, 672–678; Halstead et al., 1984, Am J Trop Med Hyg 33, 679–683; Eckels et al, 1984, Am J Trop Med Hyg 33, 679–683).

Adaptation of PDK-passaged viruses to FRhL was uniformly successful for all strains of DEN virus and was not dependent on PDK passage. Viral titers from harvests of FRhL passages 1–4 ranged from $10^5$–$10^6$ PFU/ml. By the third-forth FRHL passage, vaccine lots of all of the DEN strain set viruses were prepared and tested as listed in Table 2. Data is also provided in Table 2 for the FRhL cell bank testing as well as the master and production seed testing. Results of these tests, required to ensure the safety and the freedom from contamination, were negative, or fell within allowable specifications. For the DEN-4 341750 PDK-20 production seed, monkey neurovirulence tests were performed. Results of this study can be found in Hoke, 1990 (Am J Trop Med Hyg 43, 219–226). The DEN-4 production seed as well as the DEN-4 parent virus that was used for comparison were not neuropathogenic. Whether the remaining candidate DEN vaccines need to be evaluated for neurovirulence remains questionable based on data from this experience as well as other tests of DEN monkey neurovirulence (personal comunication).

EXAMPLE 2

Rhesus monkeys inoculated with PDK-passaged DEN viruses. The infectivity of DEN viruses passaged in PDK cells and designated as "strain sets" was compared to parental, unmodified viruses for each serotype. Table 3 lists the results of these studies where the degree of infectivity for monkeys was measured by the number of days of viremia that could be found in sequentially drawn serum two weeks following inoculation. Parental virus inoculation of monkeys resulted in 6.8, 5, 3, and 4.7 mean days of viremia in groups of 3–4 monkeys inoculated with DEN-1, DEN-2, DEN-3, and DEN-4, respectively. For DEN-2 parent, additional data (not shown) has substantiated that infection with measurable viremia is very reproducible over time using similar monkeys and isolation techniques. Unfortunately, only partial data exists on viral titers in monkey sera. Most of the data that exists comes from experience with the DEN-2 parent virus where monkey viremic blood was titrated in mosquito cell culture. Peak viral titers at 4–8 days post inoculation resulted in titers reaching $10^5$ PFU/ml of serum (Putnak et al, 1996, supra).

For each strain set, PDK passage results in modification of DEN virus as shown by reduced capacity of the virus to infect monkeys. For several of the strain sets this was clearly evidenced by the complete lack of viremia at the highest PDK passage. Inoculation of monkeys with DEN-1 at PDK passage 27 resulted in 0 days of viremia in 4 monkeys. This translates to 0 isolations out of a total of 56 bleedings tested. A similar result was found for DEN-3 PDK-20 and PDK-30. At PDK-30 for this virus, all evidence of monkey infectivity was lost, i.e., no viremia and no evidence of seroconversion in the monkeys inoculated with $10^6$ PFU of virus. The DEN-2 strain required the greatest number of PDK passages to attain modification of monkey infectivity. With this virus, at least 40 passages in PDK cell culture were required for reduced viremia. To contrast this experience, the DEN-4 strain 341750 only required 6 passages in PDK cells for a modified monkey infection. For another DEN-1 strain, 1009, even after 50 PDK passages there was no evidence of modified monkey infection when compared to parental virus (data not shown). In conclusion, PDK cell passage appears to be an effective empirical method for modification and attenuation of various DEN isolates. This is an unnatural host for DEN that probably places selection pressure for virus populations that are suited for PDK replication but not necessarily for replication in target cells in monkeys and humans.

Materials and Methods for Candidate Vaccine Studies in Humans

Volunteers. Healthy male and female volunteers ages 18–45 were examined and screened by a panel of tests, including blood chemistries, hematology, prothrombin time, partial thromboplastin time, urinalysis, rapid plasma reagin antibody, and serology for hepatitis B surface antigen and antibody to HIV. Volunteers were excluded on the basis of persistent significant abnormality or positive test. Female volunteers were eligible to participate if they had a negative pregnancy test within 48 hours of vaccination and were willing to sign a consent form stating that they avoid conception using conventional contraception for the 3 months following vaccination. In addition, volunteers were excluded if they had previous flavivirus immunity, which may affect responses to dengue vaccines [Scott, 1983, J Infect Dis 148, 1055–1060] or a history of allergy to neomycin, streptomycin, or gentamycin. Prior flavivirus immunity was defined as having no detectable hemagglutination inhibition antibodies (at a 1:10 serum dilution) against dengue types 1–4, Japanese encephalitis, or yellow fever and no history of yellow fever vaccine or flavivirus infection.

Volunteers scored ≧70% on a written exam designed to test knowledge of all aspects of the clinical trial. Informed consent was subsequently obtained from each volunteer in compliance with US 21 CFR Part 50-Protection of Human Subjects. The clinical protocol conformed to all relevant regulatory requirements, including the Declaration of Helsinki (Protocol), and Army Regulations 70-25-Use of Volunteers as Subjects of Research, and 40-7-Use of Investigational Drugs in Humans and the Use of Schedule I Controlled Substances. The studies were approved by the Human Subject Research Review Board, Office of the Surgeon General, U.S. Army, the WRAIR Human Use Research Committee, and the Institutional Review Board, University of Maryland at Baltimore.

Study Vaccines. The study vaccines are listed in table 4. Vaccine viruses were passaged repeatedly in primary dog kidney cells and then in fetal rhesus monkey lung (FRhL) continuous diploid cell culture as three terminal passages to prepare seed and vaccine. Each candidate, before trial in volunteers, was confirmed to elicit substantially reduced viremia compared to its wild-type parent virus in vaccinated rhesus monkeys. Adequate attenuation measured by infection of rhesus monkeys indicated that the dengue vaccine strains were appropriate vaccines for human testing.

Immediately before immunization, a vial of lyophilized vaccine was reconstituted with sterile water for injection (USP). After immunization, unused portions of rehydrated vaccine were maintained on ice and titrated within 4 hours in LLC-$MK_2$ cell monolayers (Sukhavachana et al. 1966, Bull WHO 35, 65–66). Each volunteer received between $1.0\times10^5$ and $4.5\times10^6$ pfu of virus, depending on the candidate vaccine injected (Table 4). The passage history of the individual study vaccines is summarized below.

TABLE 4

WRAIR LIVE ATTENUATED DENGUE VACCINES

| Vaccine | PKD Passage* | Year | Study Site | Number of Volunteers | Dose ($\times10^5$ pfu) |
|---|---|---|---|---|---|
| Dengue 1 | 27 | 1991 | CVD | 10 | 4.4–45 |
| (45AZ5) | 20 | 1991<br>1992 | CVD # | 10 | 7.7–38 |
| | 10 | 1991<br>1992 | CVD | 9 | 2.8–3.5 |
| | 0 | 1984 | USAMRIID ## | 2 | ? |

TABLE 4-continued

WRAIR LIVE ATTENUATED DENGUE VACCINES

| Vaccine | PKD Passage* | Year | Study Site | Number of Volunteers | Dose (×10$^5$ pfu) |
|---|---|---|---|---|---|
| Dengue 2 | 50 | 1991 | CVD | 3 | 6.8 |
| (S16803) | 40 | 1996 | USAMRIID | 3 | 5 |
|  | 30 | 1991 1992 | CVD | 10 | 5.6–10 |
| Dengue 3 | 20 | 1992 | CVD | 6 | 1.0–1.4 |
| (CH53489) | 10 | 1992 | CVD | 3 | 3.8 |
|  | 0 | 1986 | USAMRIID | 2 | ? |
| Dengue 4 | 20 | 1989 | USAMRIID | 8 | 1.0 |
| (341750) | 15 | 1991 | CVD | 3 | 4.8 |
| TOTAL | 10 | — | — | 69 | — |

*Primary dog kidney passage level
Center for Vaccine Development, University of Maryland, Baltimore
United States Army Medical Research Institute of Infectious Diseases, Frederick, MD Dengue 1 45AZ5 Vaccine: DEN-1 strain West Pac 74 was isolated from a human case of DEN fever on Nairu Island (Western Pacific) in 1974. The isolate was passaged 20 times in FrhL cell culture and a vaccine lot was prepared. Passages included mutagenization and plaque selection to recover a virus that was attenuated and suitable for human vaccination. Following vaccination of two human volunteers, the decision was made to discontinue use of the vaccine due to DEN illness in one of the volunteers. The vaccine was further attenuated by passage in PDK and FrhL cell cultures. The current, candidate vaccine is DEN-1 45AZ5 PDK-20.

Denaue 2 S16803 Vaccine: The dengue 2 strain S16803 virus was derived from a Thai virus isolate from a patient with dengue fever. The virus was subjected to a total of 50 PDK passages, with terminal passage in fetal rhesus monkey lung diploid cells (DBS-FRhL-2) for seed and vaccine production. Two vaccine candidates were initially prepared at the 30th and 50th PDK passage levels and selected for testing. Another vaccine candidate was developed at the WRAIR from the same dengue 2 parent strain S16803 virus and produced at the 40th passage level by the Salk Institute (Swiftwater, Pa.).

Denaue Type-3 CH53489 Vaccine: Dengue type-3 strain CH53489 virus was derived from a Thai strain, passaged 30 times in primary dog kidney (PDK) cells after initial passage in primary green monkey kidney (PGMK) and C6/36 insect cells. Virus from PDK passages 10, 20, and 30 was used to inoculate fetal rhesus monkey lung diploid cell cultures.

Denaue 4 341750 Carib Vaccine: The dengue 4 vaccine candidate was derived from a Caribbean strain of Dengue 4 (Columbia, 1982), passaged at the University of Hawaii, and manufactured at the WRAIR [Marchette, 1990, Am J Trop Med Hyg 43, 212–218]. Antibody to the parent virus neutralizes other dengue 4 virus strains including H-241, the prototype strain. Attenuation of the human isolate was achieved by passage 20 times in primary canine kidney (PDK) cell cultures.

Study Design. A standard randomized, single-blind inpatient clinical protocol was used for all pilot studies. The majority of the studies were conducted at the Center for Vaccine Development, University of Maryland, Baltimore Md. The pilot studies of dengue 2 S16803 PDK 40 vaccine and dengue 4 CH341750 PDK 20 vaccine were performed at the Medical Division, United States Army Medical Research Institute of Infectious Diseases (USAMRIID), Ft Detrick, Md.

In the initial clinical studies of a vaccine, the highest available passage for a particular strain was tested first in three volunteers. Symptoms were monitored closely for three weeks, and if the volunteers remained well, the next lower passage was tested. If one or more of the volunteers became ill, testing of lower passages of the vaccine strain was not performed, as it was presumed lower passages were likely to be less attenuated. After testing of all acceptable passage levels in three volunteers, the lowest level that did not cause illness was selected for further testing in up to seven additional volunteers.

To allow careful observation, prevent exposure to extraneous infectious diseases, and to prevent the possible infection of vector mosquitoes, volunteers were confined to the research ward from three days prior to inoculation until 20 days after immunization. All adverse experiences occurring within this period following administration of each vaccine were recorded, irrespective of severity or whether or not they are considered vaccination-related. Acceptable safety of a vaccine was defined in advance as the absence of the following serious adverse events: any severe clinical illness not explained by a diagnosis unrelated to the vaccination; persistent fever (oral temperature of $\geq 38.5°$ C. for 4 determinations over 24 hours, a maximum daily oral temperature of $\geq 38.5°$ C. on three successive days, or temperature exceeds 40° C. on any individual determination); thrombocytopenia (fewer than 100,000 platelets/mm$^3$) or leukopenia (absolute neutrophil count<1000) on 2 consecutive determinations; or serum amino alanine transferase (ALT) level of more than 4 times normal on 3 or more successive days which is otherwise unexplained. In addition, any experience which would suggest any significant side effect that may be associated with the use of the vaccine were documented as a serious event.

Volunteers were inoculated subcutaneously with 0.5 ml of undiluted vaccine on day 0. After immunization, vital signs were recorded every 6 hours. The injection site was examined and the maximum diameter of erythema and induration measured and recorded daily. Clinical signs (fever [>37.8° C.], rash, vomiting, petechiae, and liver and splenic enlargement) and symptoms (malaise, headache, myalgia, arthralgia, nausea, and eye pain or photophobia) were assessed daily for the first 20 days after immunization. Symptoms were graded as mild (noticed symptom but continued ward activity) or severe .(forced to bed by symptom). If requested by the volunteer, painful symptoms were treated with propoxyphene hydrochloride; antipyretics were not used. Observations were recorded on a standard checklist of symptoms and physical findings. Volunteers were discharged from the study ward on day 21, and requested to return for serologic studies 1, 6, 12, and 24 months after inoculation.

Two healthy flavivirus-immune volunteers were immunized at USAMRIID with the parent strain of the dengue 1 45AZ5 vaccine and two years later with the parent strain of the dengue 3 CH53489 vaccine. Medical records from the study were reviewed for presence or absence of the following signs and symptoms: fever, rash, malaise, headache, myalgia, arthralgia, and eye pain or photophobia. Viremia was measured daily. In contrast to the present trials, symptoms were not systematically recorded, and the intensity of symptoms was not graded. In addition, clinical experience with the dengue 4 341750 Carib PDK 20, given to 8 volunteers at USAMRIID during a later study, was extracted and summarized to compare with those of the current vaccinees [Hoke, 1990, supra].

Laboratory Evaluation. Blood was collected from volunteers every other day and on day 31 for routinely available medical tests for hemoglobin and hematocrit, white blood cell count with differential count, platelet count, and aspartate aminotransferase (AST) and alanine aminotransferase (ALT) levels. In addition, blood was collected every other day through day 20 for virus isolation and antibody studies. Blood (20 ml) was allowed to clot at 4° C. for $\leq 2$ hours, sera was decanted into 1-ml aliquots, frozen and stored at −70° C. until study.

Virus Isolation. For determination of dengue viremia, serum was thawed and inoculated onto C6/36 mosquito cell monolayers and incubated at 28° C. for 14 days. Supernatant culture fluid harvests were assayed for virus by plaque assay on LLC-MK$_2$ cells (Sukhavachana et al. 1966, Bull WHO 35, 65–66). To quantitate the amount of virus in serum, a plaque assay was performed on the C6/36 clone of Aedes albopictus mosquito cells [Hoke, 1990, supra]. Cell culture flasks were inoculated with dilutions of plasma and adsorbed at 35° C. for 1–2 hours. An overlay medium consisting of Hank's Balanced Salt Solution and 0.75% agarose, 5% lactalbumin hydrolysate, 0.12 M NaHCO$_3$, and antibiotics was added and all flasks were incubated at 35° C. After 7 days, the flasks were stained with 5% liquid neutral red for 3–5 hours. Excess stain was removed and the plaques read after 18 hours.

Serology. Antibody tests included ELISA, HAI, and plaque reduction neutralization tests (PRNT) performed using a dengue virus of the same serotype as the strain in the vaccine being tested. Detection of anti-dengue IgM antibodies was performed by modification of an ELISA, where values >0.10 OD units were considered positive [Innis, 1989, supra]. The HAI test was performed by the standard technique modified to microvolumes using 4–8 units of individual antigens, using serum extracted with acetone to remove inhibitors [Clarke and Casals, 1958, Am J Trop Med Hyg 7, 561–573]. PRNT assays were performed by the method described by Russell et al. [Russell, 1967, supra].

Statistical Analysis. The relationship between passage level and the frequency and severity of reactogenicity was analyzed, for dengue 2 vaccine S16803 (PDK 30, 40 and 50) and for dengue 3 vaccine CH53489 (PDK 10 and 20), using the Cochran-Armitage test for trend and Spearman's correlations, respectively. The symptoms and signs independently analyzed included the presence or absence, and the number of days experiencing eye symptoms, headache, malaise, myalgia, arthralgia, rash and fever (temperature>37.8° C.). The null hypothesis, that higher PDK level was not associated with lower reactogenicity, was evaluated at a probability of five percent. By inspection of the data, the optimal passage level for each virus was determined based on the clinical and immunological responses of each volunteer. The passage level which caused no unacceptable side effects but which immunized about 80% of volunteers was selected for further development by the U.S. Army Medical Research and Development Command's Flavivirus Vaccine Steering Committee.

Definition of Infection by the Vaccine

Infection by vaccine is defined as replication of dengue virus in the volunteer, detected by presence of serum type-specific neutralizing antibody or IgM anti-dengue antibody after immunization. Viremia was not included as necessary for diagnosis of infection as it was never detected in the absence of an antibody response. A vaccine failure is defined as an unacceptable adverse clinical response or failure to develop convalescent IgM or PRNT antibodies.

EXAMPLE 3

Clinical Responses to Attenuated Denaue Vaccines Dengue 2 S16803 Vaccine

The dengue 2 strain S16803 virus produced from the 50th passage in PDK cells was tested in three volunteers. The volunteers did well, with no oral temperatures >38.0° C. Two of 3 volunteers had transient mild symptoms of malaise, headache, and eye symptoms (eye pain or photophobia). Laboratory findings included mild ALT elevations (<2×normal) in 2 of 3, and mild leukopenia in 1 of 3 volunteers. Because of the acceptable safety profile of the PDK 50 vaccine, the next lower available passage, PDK 30, was selected for clinical evaluation.

The PDK 30 vaccine, tested in 10 subjects, was underattenuated and produced symptoms compatible with mild to moderate dengue. Four volunteers (40%) developed low grade fever, to Tmax 38.5° C., over days 9 . 14 post vaccination (median day 12). Eighty percent developed rash. The majority of volunteers experienced eye symptoms (10/10), headaches (9/10), and malaise (9/10), while 70 percent had ≧1 severe symptom of headache, eye pain and photophobia, malaise, or myalgia. Three volunteers had mild elevation of their alanine aminotransferase (ALT), a measure of liver pathology.

Because the PDK 30 vaccine was considered too reactogenic to test further in volunteers, the PDK 40 vaccine was produced from the master seed. Two of three volunteers inoculated with PDK 40 developed a mild dengue-like syndrome 9–10 days after vaccination, with low-grade temperatures (<38.1° C.), rash, myalgias, and headache. Symptoms resolved spontaneously over several days without disability or requirement for medication. Accompanying symptoms was an unanticipated rise in serum liver enzymes, to a maximum ALT level of 199 IU/ml in one (4 times normal) and 77 IU/ml maximum ALT for the other (1.5 fold elevation from normal). The third volunteer remained asymptomatic but also developed two-fold elevations in ALT (to max $10^2$). All laboratory abnormalities resolved within days without intervention, and all volunteers were discharged in good health 21 days after receipt of the vaccine. Because of the unusual frequency of hepatitis events associated with PDK 40 vaccine, no further development is planned for the product.

Table 5 summarizes the initial clinical experience with the WRAIR dengue 2 vaccine. Decreased frequency of signs of fever and rash are apparent between passage level 30 and 50 vaccines. Furthermore, there is a decline in oral temperature from Tmax 38.5° C. towards normal with increasing passage, but no change in duration of fever beyond one day. For the dengue 2 vaccine, the frequency and duration of eye symptoms, rash, headache, malaise and myalgia were significantly associated with passage level.

TABLE 5

Clinical Responses in Recipients of Dengue 2 S16803 Virus Vaccines

| Passage Level | malaise | headache | myalgia | arthralgia | eye sx | rash | fever T > 37.8∝C | days of fever (median) | max fever |
|---|---|---|---|---|---|---|---|---|---|
| 2-S16803-30 | 9/10 | 9/10 | 7/10 | 4/10 | 10/10 | 8/10 | 4/10 | 9–14 (12) | 38.5 |
| 2-S16803-40 | 2/3 | 2/3 | 2/3 | 1/3 | 1/3 | 2/3 | 1/3 | 8, 9 | 38.0 |
| 2-S16803-50 | 2/3 | 2/3 | 0/3 | 1/3 | 2/3 | 0/3 | 0/3 | — | — |

TABLE 5-continued

Clinical Responses in Recipients of Dengue 2 S16803 Virus Vaccines

Symptom - days

| Passage Level | malaise | headache | myalgia | arthralgia | eye sx | rash | fever T > 37.8°C |
|---|---|---|---|---|---|---|---|
| 2-S16803-30 | 2.2 | 3.6 | 2.4 | 1.7 | 3.3 | 5.4 | 0.5 |
| 2-S16803-40 | 2.0 | 1.7 | 2.0 | 1.0 | 5.7 | 1.7 | 0.7 |
| 2-S16803-50 | 0.6 | 0.7 | 0.0 | 0.3 | 1.0 | 0.0 | 0.0 |

TABLE 6

Clinical Responses in Recipients of Dengue 3 CH53489 Virus Vaccines

A: Number of patients having response

| vaccine | malaise | headache | myalgia | arthralgia | eye sx | rash | T > 37.8 °C (days) | max fever |
|---|---|---|---|---|---|---|---|---|
| 3-CH53489-0 | 2/2 | 2/2 | 2/2 | 1/2 | 2/2 | 2/2 | 2/2 (5–9) | 40.6 |
| 3-CH53489-10 | 1/3 | 2/3 | 2/3 | 1/3 | 1/3 | 2/3 | 1/3 (10, 11) | 38.2 |
| 3-CH53489-20 | 3/6 | 5/6 | 3/6 | 4/6 | 4/6 | 1/6 | 1/6 (3) | 38.7 |

B: Symptom days

| vaccine | malaise | headache | myalgia | arthralgia | eye sx | rash | T > 37.8 °C (days) |
|---|---|---|---|---|---|---|---|
| 3-CH53489-0 | 3.5 | 4.0 | 4.5 | 2.0 | 3.5 | 7.5 | 5.0 |
| 3-CH53489-10 | 0.3 | 3.3 | 2.3 | 1.0 | 1.3 | 6.3 | 0.7 |
| 3-CH53489-20 | 1.7 | 2.8 | 1.0 | 2.0 | 1.3 | 0.8 | 0.2 |

TABLE 7

Viremia and Immune Responses to Dengue Vaccines

| Vaccine and passage level | viremia | days of viremia (median) | range titer | seroconversion IgM | HAI | PRNT | GMT31 | GMT60 |
|---|---|---|---|---|---|---|---|---|
| 2-16803-30 | 10/10 | 6–12 (10) | 3–1200 | 8/10 | 6/9 | 10/10 | 343 | 262 |
| 2-16803-40 | 2/3 | 6–10 (8) | NA | 3/3 | 2/3 | 3/3 | 640 | 618 |
| 2-16803-50 | 0/3 | — | — | 1/3 | 1/3 | 2/3 | 11 | 13 |
| 3-53489-0 | 2/2 | 3–10 (6) | NA | 2/2 | 2/2 | 2/2 | 2818 | 1995 |
| 3-53489-10 | 2/3 | 6–10 (8) | 84–6600 | 1/3 | 3/3 | 3/3 | 710 | 153 |
| 3-53489-20 | 2/6 | 8–12 (10) | 12–138 | 2/6 | 1/6 | 3/6 | 556 | |
| 4-341750-15 | 1/3 | 8–10 (9) | 3–15 | 3/3 | 3/3 | 3/3 | | |
| 4-341750-20 | 5/8 | 8–14 (10) | 10–1200 | 5/8 | 5/8 | 5/8 | | 160 |

TABLE 8

Results of Phase I Trials of WRAIR Dengue Vaccine Candidates

| Vaccine | PDK Passage[a] | Mean Days viremia | Mean Illness Score | Acceptable Reactogenicity | Number Infected[b] | Number Seroconverted[c] | Range % Seroconversion |
|---|---|---|---|---|---|---|---|
| Dengue 1 (45AZ5) | 27 | 0.0 | 2.4 | Yes | 7 (70%) | 4 (40%) | 3–77 |
| | [20] | 1.0 | 3.6 | Yes | 10 (100%) | 10 (100%) | |
| | 10 | 5.0 | 3.9 | Yes | 7 (78%) | 7 (78%) | |

TABLE 8-continued

Results of Phase I Trials of WRAIR Dengue Vaccine Candidates

| Vaccine | PDK Passage[a] | Mean Days viremia | Mean Illness Score | Acceptable Reactogenicity | Number Infected[b] | Number Seroconverted[c] | Range % Seroconversion |
|---|---|---|---|---|---|---|---|
| Dengue 2 | [50] | 0.0 | 5.0 | Yes | 2 (67%) | 2 (67%) | |
| (S16803) | 40 | 1.7 | 14.7 | No | 3 (100%) | 3 (100%) | |
| | 30 | 2.2 | 19.1 | No | 10 (100%) | 10 (100%) | |
| Dengue 3 | [20] | 0.6 | 11.0 | Yes | 3 (50%) | 3 (50%) | |
| (CH53489) | 10 | 2.3 | 15.3 | No | 3 (100%) | 3 (100%) | |
| Dengue 4 | [20] | 3.8 | 6.6 | Yes | 5 (63%) | 5 (63%) | |
| (341750) | 15 | 0.6 | 20.7 | No | 3 (100%) | 3 (100%) | |

[a]Primary dog kidney passage level
[b]Defined as anti-dengue IgM positive or PRNT50 seroconversion
[c]Defined as a neutralizing antibody titer >1:10 (PRNT50)
[ ]Strain proposed for expanded clinical study Dengue 3 CH53489 Vaccine. A dengue 3 vaccine (CH53489, PDK 0) developed at WRAIR was administered to two healthy yellow fever-immune male volunteers as a 0.5 ml subcutaneous inoculation of $2 \times 10^4$ pfu of virus. The immediate post immunization course was uneventful. By day 6, both volunteers were ill with moderately severe dengue fever characterized by high fever, chills, myalgias, headache, malaise, and a diffuse erythematous rash. Both volunteers developed thrombocytopenia and leukopenia but there were no signs of hemorrhagic fever. After a febrile period lasting five days, both men rapidly recovered and were well by day 21. Because of the severe illnesses experienced by both subjects, no further testing of this passage level was undertaken. Subsequently, PDK 10 and PDK 20 passage levels were prepared as vaccine candidates.

The PDK 20 vaccine was given to 6 volunteers and resulted in mild reactogenicity. One subject experienced an early febrile illness on day 3 with transient fever (Tmax 38.2° C.), pharyngitis, and cervical lymphadenopathy. No dengue virus was isolated from the volunteer's serum. This subject was felt to have had an intercurrent illness with fever, which was not directly related to vaccination. Four out of 6 volunteers developed short-lived mild dengue symptoms without rash; arthralgia, eye pain, and headache were the most frequent complaints. However, one volunteer had more severe symptoms of headache, malaise, and eye pain for three days. He also developed leukopenia and sustained elevation in ALT levels; these laboratory abnormalities had resolved on follow-up at day 31. Another volunteer had mild and reversible elevation of ALT alone, to less than 2×normal. Because the PDK 20 vaccine was safe with marginally acceptable reactogenicity, the next lowest available passage vaccine virus (PDK 10) was tested.

The PDK 10 virus proved too reactogenic in recipients. One of three volunteers developed low-grade fever on days 10 and 11 (Tmax 38.3° C.), and a florid rash for 13 days. Another volunteer developed persistent pruritus associated with waxing and waning hives on days 6 to 9 post vaccination, and tender cervical and axillary lymph nodes. He subsequently developed a maculopapular rash with malaise, headache, and myalgia on days 10–12. This volunteer may have had an idiosyncratic allergic reaction to the vaccine, followed by a typical dengue-like illness. These two volunteers also had laboratory abnormalities of leukopenia and elevation of ALT levels to <2×normal, which resolved on followup on day 31.

Table 6 summarizes the response to dengue 3 CH53489 vaccines. Although there was a trend for less frequent and shorter duration signs and symptoms with passage, no passage reached statistical significance in either analysis.

Dengue 4 341750 Vaccine. Eight volunteers received $10^5$ PFU of PDK 20 vaccine [Hoke, 1990 supra]. Five volunteers developed a scarcely noticeable macular, blanching rash and minimal temperature elevation (max 38.1° C.). Viremia and antibody response also developed in these five volunteers (63%).

A new DEN-4 341750 candidate vaccine was prepared from PDK passage 15, anticipating that the lower passage might be more infective. Three volunteers received this vaccine and two experienced minimal symptoms. The third volunteer became ill abruptly on day 8 with fever, edematous swelling of the face and extremities, severe lassitude, rash, eye pain, photophobia, and arthralgias. Over the next three days, fever persisted with Tmax of 39.6° C., but signs and symptoms resolved spontaneously. Because of this serious adverse reaction to vaccination, further use of PDK-15 vaccine was terminated and PDK-20 was chosen for further evaluation.

EXAMPLE 4

Viremia and Immune Responses to Attenuated Dengue Vaccines

Table 7 describes viremia and immune responses with the WRAIR dengue vaccines. The infectivity of the individual vaccines is summarized below.

Dengue 2 S16803 Vaccine. No recipients of the PDK 50 vaccine developed viremia, yet two of 3 developed low-titer neutralizing antibody by day 60. These findings suggested that the vaccine virus was diminished in infectivity for humans. By contrast, two of 3 dengue 2 PDK 40 vaccinees had demonstrable viremia, and all developed high titer antibody after vaccination. As expected, infectivity of the dengue 2 PDK 30 vaccine was highest: viremia was detected in all 10 volunteers and all subjects seroconverted with neutralizing antibody titers of >1:60 by day 60.

Dengue 3 CH53489 Vaccine. Dengue-3 virus retaining temperature sensitivity and small plaque phenotype of the vaccine virus was recovered for 6 and 7 days in the 2 yellow fever immune recipients of the dengue 3 PDK 0 vaccine. Subsequently, high titered PRNT50 and hemagglutination inhibition (HAI) antibodies with a secondary-infection-like cross reactivity was measured in serum collected on days 30 and 60 from both volunteers. Infectivity was similar in subjects who received the dengue 3 PDK 10 attenuated vaccine: 2 of 3 developed viremia and vaccination induced neutralizing antibodies in all. In contrast, 2 of 6 dengue 3 PDK 20 vaccinees had detectable viremia and three volunteers subsequently seroconverted, reflecting diminished infectivity.

Dengue 4 341750 Vaccine. Eight volunteers received $10^5$ PFU of the PDK 20 vaccine, and viremia and antibody response developed in five (63%). The vaccine prepared from a lower passage of this candidate, PDK 15, was more infective. Virus was isolated from a single volunteer, on days 8 and 10 following vaccination, with maximum titer of 15 pfu/ml. This volunteer subsequently developed a neutralizing antibody titer of 450 with a secondary HAI response, and was found to have been previously exposed to St. Louis encephalitis virus (PRNT titer 1:20 before vaccination). The two volunteers without detectable viremia developed neutralizing titers of 1:10 and 1:40 by day 30 after vaccination.

EXAMPLE 5

Selection of Candidate Vaccines

The extended program of safety testing of the WRAIR PDK-attenuated vaccines is shown in Table 8, which lists the salient features of the vaccines for each serotype. Increasing PDK passage resulted in decreasing mean illness score, which assesses duration and number of symptoms per volunteer. In addition, rising PDK passage was also associated with decreased mean days of viremia, with the exception of dengue 4 vaccines. Of the tested dengue 2, 3, and 4 vaccines, only one passage level was judged safe and acceptably reactogenic, and suitable for expanded clinical study: dengue 2 PDK 50, dengue 3 PDK 20, and dengue 4 PDK 20. However, the percentage of recipients infected declined with increasing PDK passage level. Seroconversion, defined as percentage with neutralizing antibody titer$\geq$1:10 similarly declined within broad confidence intervals.

Discussion

The WRAIR has longstanding involvement in the development of live-attenuated dengue vaccines. Both the WRAIR and Mahidol dengue vaccine programs have developed several live vaccines by attenuation through several passages (repeated growth in tissue culture) in dog kidney (PDK) cells. The results of the pilot testing in small numbers of volunteers established the safety of WRAIR candidate vaccines. No volunteers among 65 recipients required emergent treatment of sustained serious injury. Three volunteers suffered transient idiosyncratic reactions associated with dengue vaccination, resulting in withdrawal of the vaccines they received from further clinical development. Experimental infection with underattenuated vaccines, while uncomfortable, was tolerable.

The clinical experience showed that increasing PDK passage of vaccine viruses increased attenuation for volunteers. This effect is best seen with dengue 1 and dengue 3 viruses, where parental unpassaged viruses resulted in unmodified dengue fever and subsequent 20 PDK passages acceptable reactogenicity. However, increasing PDK passage decreased infectivity of vaccine viruses, resulting in diminished immunogenicity. Furthermore, diminished viremia with vaccine viruses in humans appear to correlate with those in rhesus monkeys (with the exception of dengue 4 PDK 15). These findings suggest that infectiousness of an attenuated dengue virus vaccine in volunteers proved equivalent to immunogenicity. The relationship between passage level and reactogenicity should be interpreted with caution, because subjects who experienced one symptom were likely to experience several symptoms. As our analytic methods assume independence of these symptoms, interpretations based on independent p-values can be tenuous. Still, we believe rash showed a strong association with passage level (independent p=0.009 for presence, p=0.01 for duration). This is bolstered by a lack of significant correlation between rash and other symptoms, for either Dengue 2 or 3 vaccine (Spearman's tests).

Only vaccines with acceptable safety profiles were selected for expanded clinical testing: dengue 1 45AZ5 PDK 20, dengue 2 S16803 PDK 50, dengue 3 CH53489 PDK 20, and dengue 4 341750 PDK 20. Because of the broad confidence intervals in seroconversion due to small numbers of volunteers, subsequent studies sought to increase the number of recipients of each of the four selected vaccines. In addition, further tests will seek to determine whether immunogenicity of these attenuated vaccines can be boosted through administration of two doses instead of the single dose used for these studies.

EXAMPLE 6

Expanded Study of Monovalent Vaccines; Monovalent Vaccines Given as Two Doses; and Monovalent Vaccines Mixed as a Tetravalent Formulation Given as One and Two Doses Study Design: The objectives of these were to evaluate the safety and immunogenicity of the four monovalent vaccines given as a single dose and then by two-dose vaccination schedules. Subsequently safety and immunogenicity of the combination tetravalent vaccine were evaluated. Subjects were separately recruited from two sites, University of Maryland at Baltimore and the WRAIR, Washington D.C. The first group of 22 subjects were divided into 4 groups of 4 or 5 persons who each received either a single dose of monovalent dengue or yellow fever 17D virus (Connaught). The 17D yellow fever vaccinees served as control and benchmark for reactogenicity. Another 31 subjects were divided into 4 groups of 7–8 persons who were given two doses of one monovalent vaccine, half at 1 month and the other half at 3 months. Finally 10 volunteers were given 2 or 3 doses of the tetravalent vaccine. The first 4 tetravalent recipients received vaccination at 0 and 1 month. The latter 6 tetravalent recipients were vaccinated at 0, 1 and 4 months. All subjects except the 10 tetravalent vaccine recipients were given a vaccine serotype at random and in double-blinded fashion.

Subjects: Subjects were normal healthy adults age 18–50. All subjects were seronegative for hepatitis B, C and HIV. All subjects were seronegative for dengue 1–4, JE, SLE, and YF by hemagglutination inhibition assay before entry into the study.

Vaccines: The four serotype vaccine candidates were originally isolated from humans with clinical disease. Each were then modified by serially passage in primary dog kidney (PDK) and then fetal rhesus lung cells as described above. These candidates were selected based on previous small pilot studies in human volunteers. Each lyophilized monovalent vaccines were reconstituted with sterile water and given in a volume of 0.5 cc. The doses of serotypes 1–4 were $10^6$, $10^6$, $10^5$ and $10^5$ pfu of Dengue 1, 2, 3, and 4 respectively. The tetravalent vaccine dose was prepared by mixing 0.25 cc of each reconstituted monovalent and given in a final volume of 1 cc. The dose of the tetravalent vaccine was 1.1–2.8×$10^6$ pfu. All vaccinations were given subcutaneously in the upper arm.

Clinical safety: Reactions to vaccinations were assessed by combination of daily symptom diaries and periodic physician evaluations during the 3 weeks after each vaccination. Subjects were housed in study quarters for close observation for 5–7 days past the incubation period of 1 week after vaccination, a time period during which reactions and viremia were most likely. Subjects were examined and queried specifically for symptoms of feverishness, chills, headache, retroorbital pain, myalgia, arthralgia, rash and others. Each symptom was graded on a scale of 0 (none), 1 (did not affect normal activity; did not require medications), 2 (required medication or change in activity), or 3 (required bedrest or unrelieved by medication). The most common symptoms were grouped into four categories. These categories were: 1)subjective fever and chills, 2)headache and retroorbital pain, 3)myalgia and arthralgia and 4)gastrointestinal complaints which included nausea, vomiting and abdominal pain. A symptom index of each category was calculated by the product of the highest symptom grade for each day and the duration of the symptom expressed in days. If symptom occurred at all during 24 hours it is assigned duration of 1 day. The Reactogenicity Index (RI) is simply the sum of the symptom indices for each category. The RI summarized the vaccine reactions of each subject. The symptom category indices and RI allow for semi-quantitative comparison of vaccine reactions among subjects and vaccine serotypes.

Subjects were monitored for hematologic and liver toxicities by serial CBC, platelet counts, AST and ALT during the study.

Serious adverse events were defined as severe illness lacking other likely causes, fever >38.5° C. continuously for over 24 hours or Tmax >38.5° C. for 3 consecutive days or a single oral temperature >104° C., neutropenia of <1,000/ml or thrombocytopenia of <90,000/ml on 2 consecutive determinations, or serum ALT or AST>5 times normal.

Immunogenicity: Method of hemagglutination inhibition assay was done by method of Clarke and Cassals, 1958 (Am J Trop Hyg 7, 561–573) Dengue IgM and IgG were measured by capture ELISA in all but the last 6 tetravalent subjects. Dengue and yellow fever neutralizing antibodies were measured on Day 0 and 30 after each vaccination by plaque reduction neutralization test. The study endpoint determination was measurement of any neutralizing antibody 30 days after last vaccination. Neutralizing antibody seroconversion is defined as 50% reduction in plaques at minimum of 1:5 serum dilution. Viremia was determined on sera from days 7–14 after initial and second vaccination. Method used for virus isolation was a delayed plaque method adapted from Yuill, 1968 (Am J Trop Med Hyg 17, 441–448) using LLC-MK$_2$ or C6/36 cells for amplification and Vero for plaque formation.

Data from the single-dose and two-dose studies were combined for this report. The subject characteristics are shown in Table 9. Total of fifty nine normal subjects were given dengue virus vaccines; forty nine received monovalent test articles and ten received tetravalent vaccine. Four received licensed 17D yellow fever vaccination (Connaught).

TABLE 9

Subject Characteristics

| Vaccine | No. Subjects (No. received 2 doses) | Sex | Race | Mean Age |
|---|---|---|---|---|
| Den-1 | 12 (8) | 7M/5F | 6W/6B | 32 |
| Den-2 | 12 (8) | 7M/5F | 7W/5B | 36 |
| Den-3 | 13 (8) | 9M/4F | 8W/5B | 36 |
| Den-4 | 12 (7) | 6M/6F | 4W/6B/1H/1AmI | 33 |

TABLE 9-continued

Subject Characteristics

| Vaccine | No. Subjects (No. received 2 doses) | Sex | Race | Mean Age |
|---|---|---|---|---|
| Tetravalent | 4 (4) | 3M/1F | 4W | 26 |
| YF 17D | 4 (0) | 3M/1F | 3W/1B | 30 |

EXAMPLE 7

REACTOGENICITY

Local reaction. Nineteen of 59 (32%) dengue vaccine recipients reported mild arm pain at injection site. Of these 7 received DEN-1, 4 DEN-2, 1 DEN-3, 1 DEN-4 and 5 received tetravalent. Only 5 reported any injection site pain after 24 hours. None affected use of the arm.

Systemic reactions. 20% of 59 dengue recipients reported no symptoms at all with their first vaccination while 70% of subjects were asymptomatic with the second vaccination. The four subjects who received a third dose reported no symptoms associated with it. The most commonly reported reactions from dengue vaccination were headache and myalgias. They occurred in varying severity. FIG. 1 shows occurrence of >Grade 1 symptoms from the first vaccination causing change in daily activities or taking of medications for relief. After the first dose of vaccine, five (8%) subjects, one serotype 1, one serotype 4, and three tetravalent, reported one severe grade 3 symptom of either chills, myalgia, headache or nausea for less than 1 day duration. No subjects reported any grade 3 symptoms with revaccination.

The RI ranged from 0 to 35. Table 10 compares the reported reactogencity of each vaccine. The DEN-1 monovalent and tetravalent vaccines were associated with more reactogenicity. The second or third dose of all dengue vaccines uniformly caused few reactions, even in those subjects with moderate to severe symptoms from the initial vaccination.

TABLE 2

Mean Reactogenicity Index

| Vaccine | Total Subjects | Dose 1 RI (n) | Dose 2 RI (n) | Dose 3 RI (n) |
|---|---|---|---|---|
| Den-1 | 12 | 7.4 (12) | 0.5 (8) | — |
| Den-2 | 12 | 3.8 (12) | 0.3 (8) | — |
| Den-3 | 13 | 2.9 (13) | 0.8 (8) | — |
| Den-4 | 12 | 3.7 (12) | 0.5 (6) | — |
| Tetravalent | 10 | 9.3 (10) | 1.9 (10) | 0.0 (4) |
| YF 17D | 4 | 3.8 (4) | — | — |

— = not done

Figure 2:
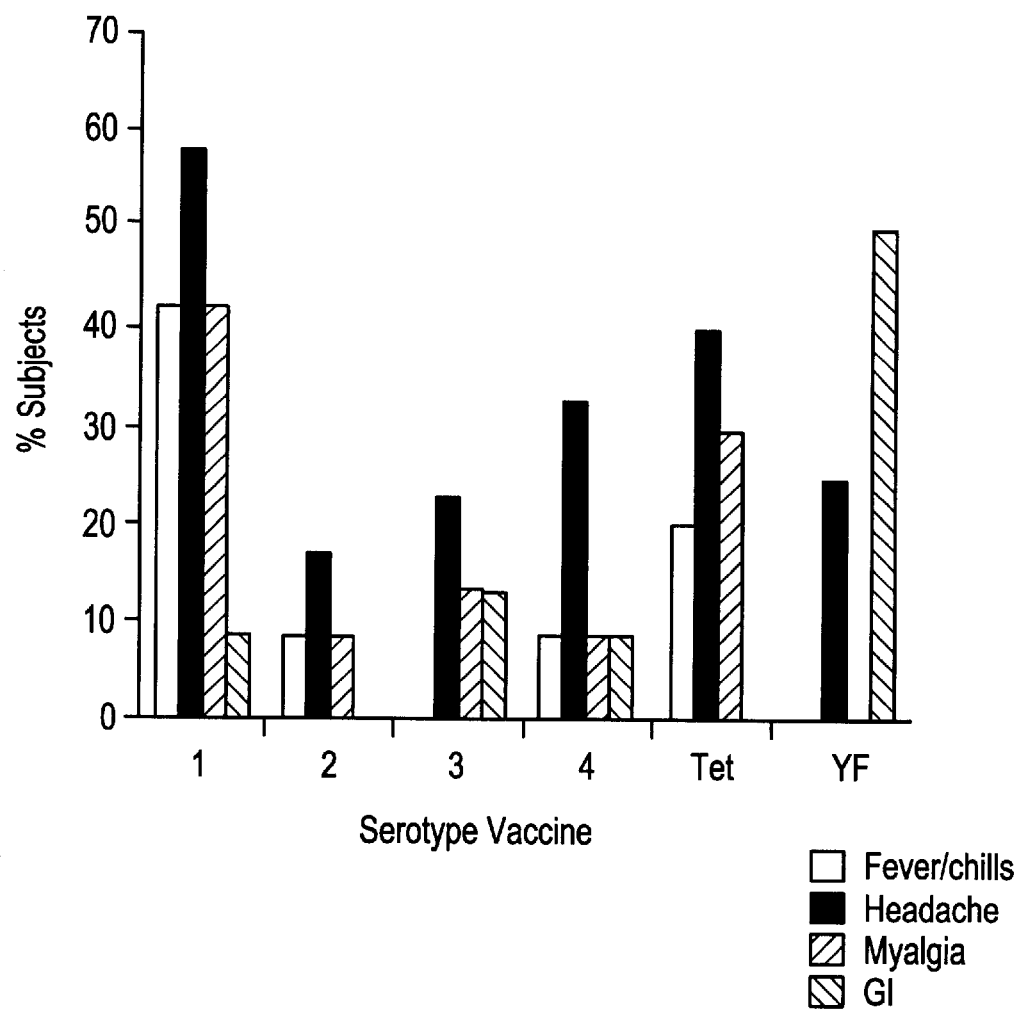
FIG. 2: Frequency of distribution of reactogenicity index by serotype.
Figure 6A:
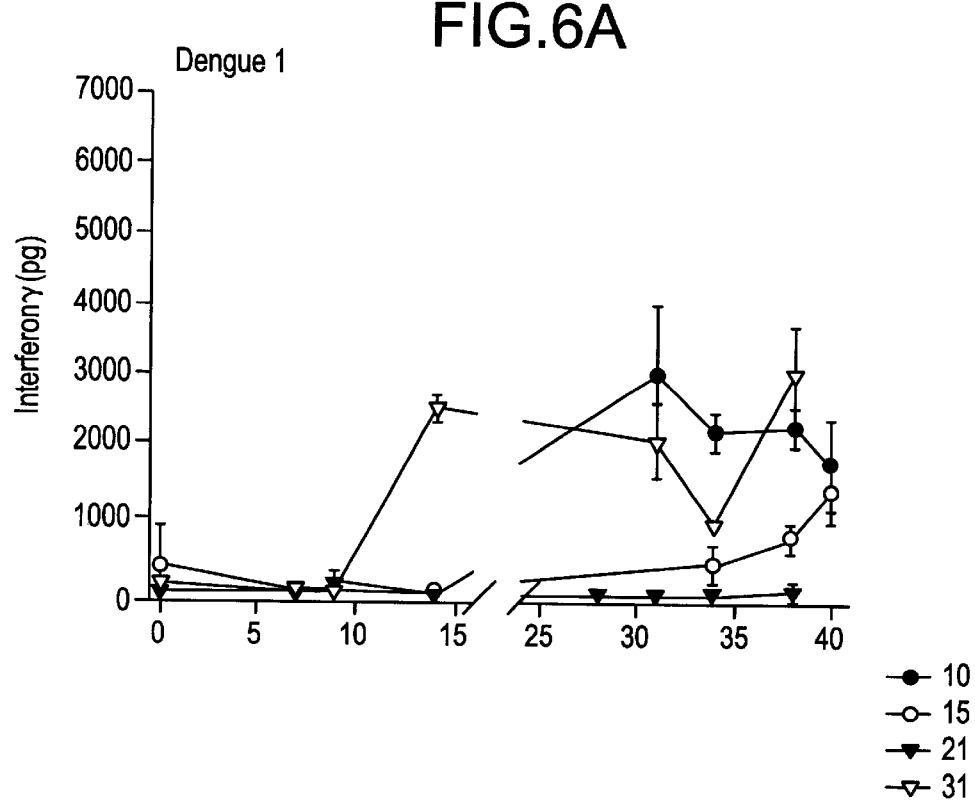
FIGS. 6A–H: Interferon γ production by PBMC collected from vaccine volunteers and stimulated with serotype specific virus. All volunteers received only one serotype of vaccine. Graphs on the left (A–D) show results from volunteers that were given the second dose around day 32. Graphs on the right (E–H) show results from volunteers that received the second dose around day 92. A response over 1000 pg/ml was seen just prior to the second dose in most volunteers. Only four volunteers had a response over 1000 pg/ml within the first 15 days of receiving the first vaccine dose.
Figure 6B:
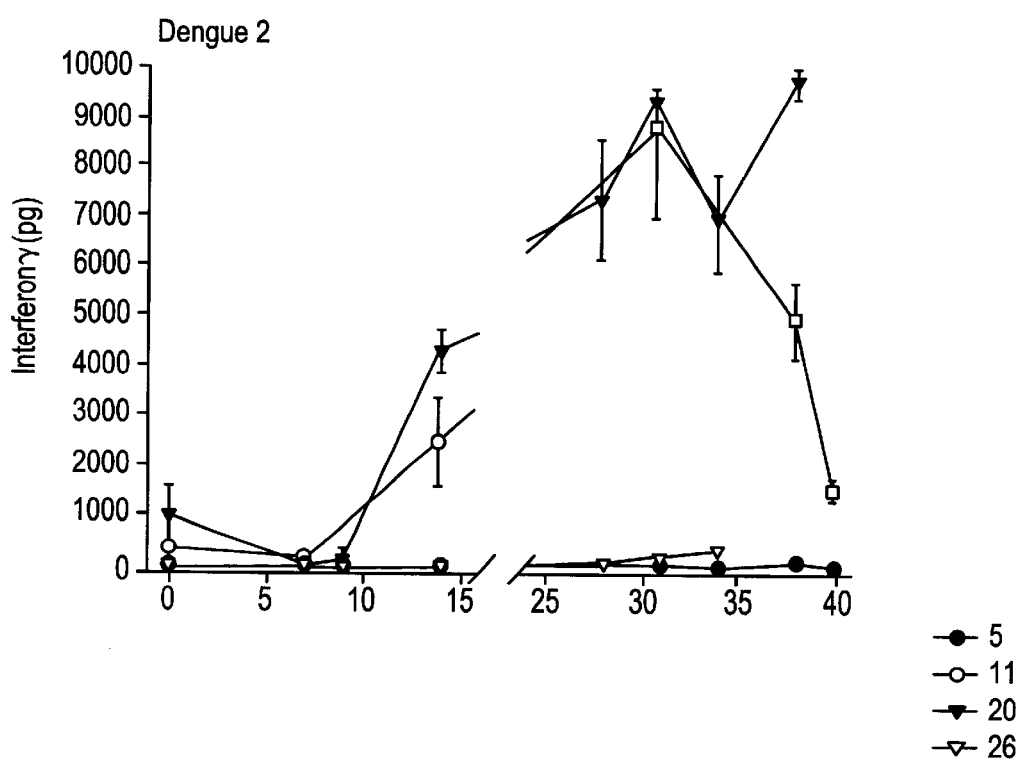
Figure 6C:
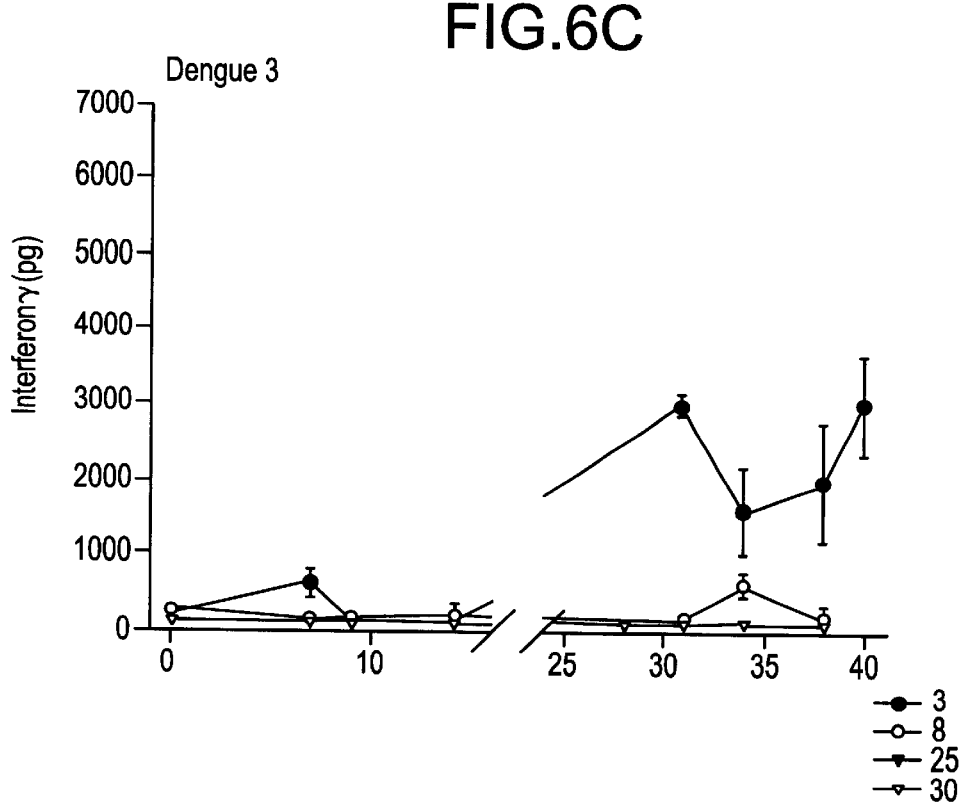
Figure 6D:
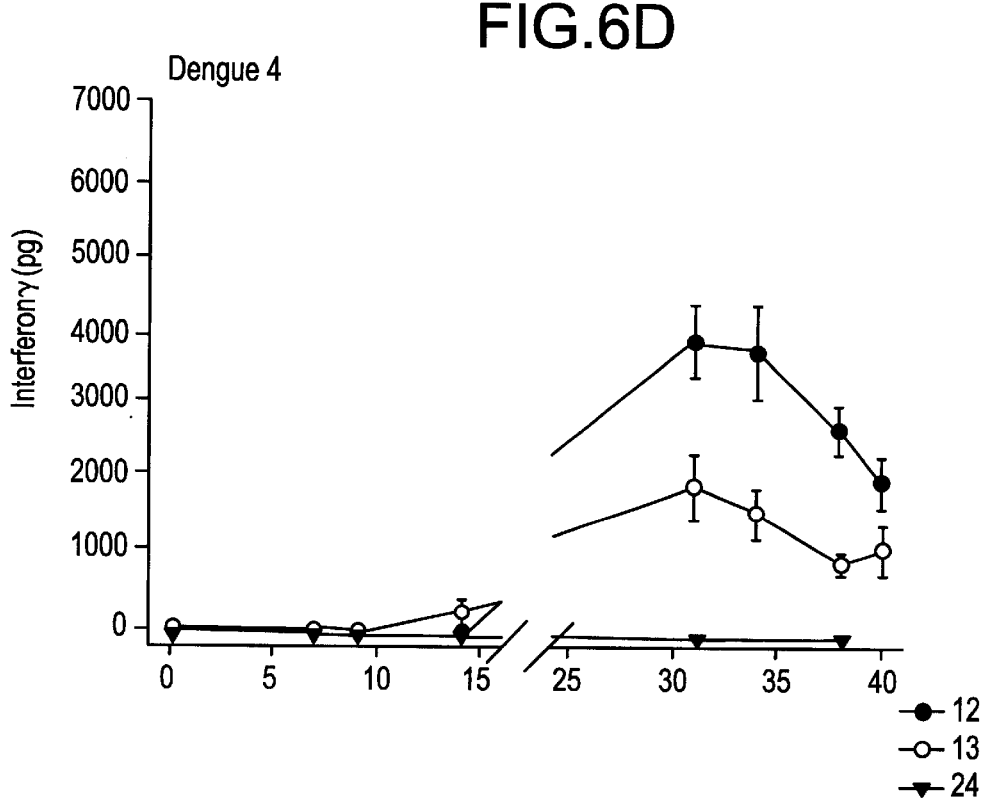
Figure 6E:
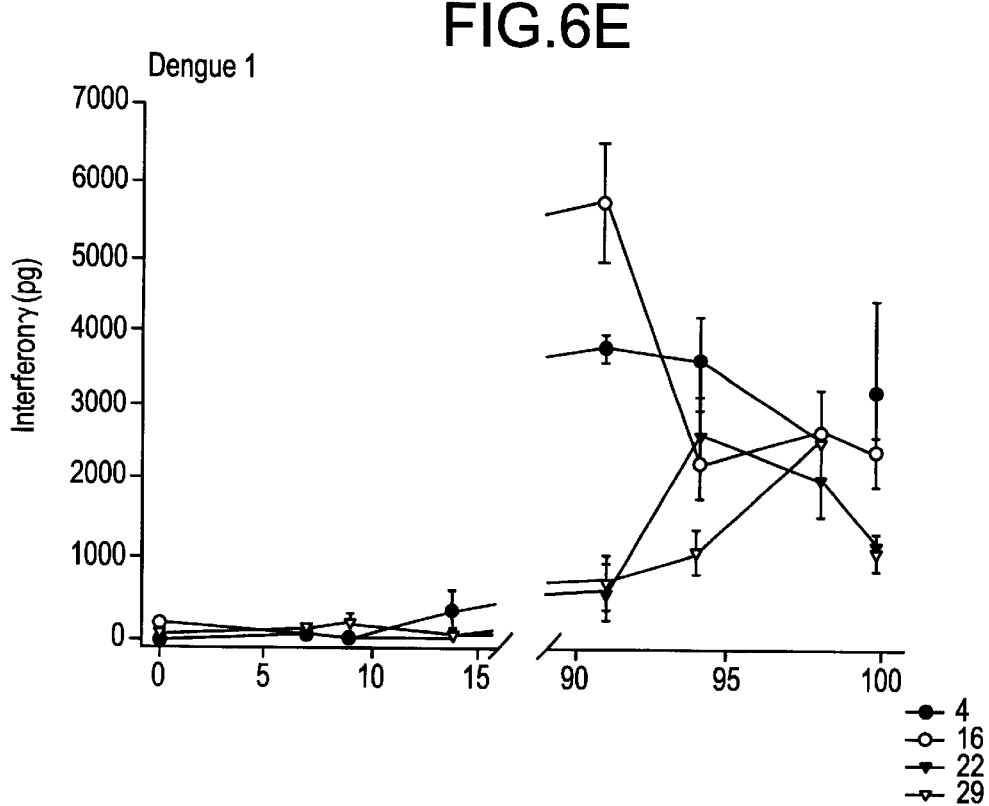
Figure 6F:
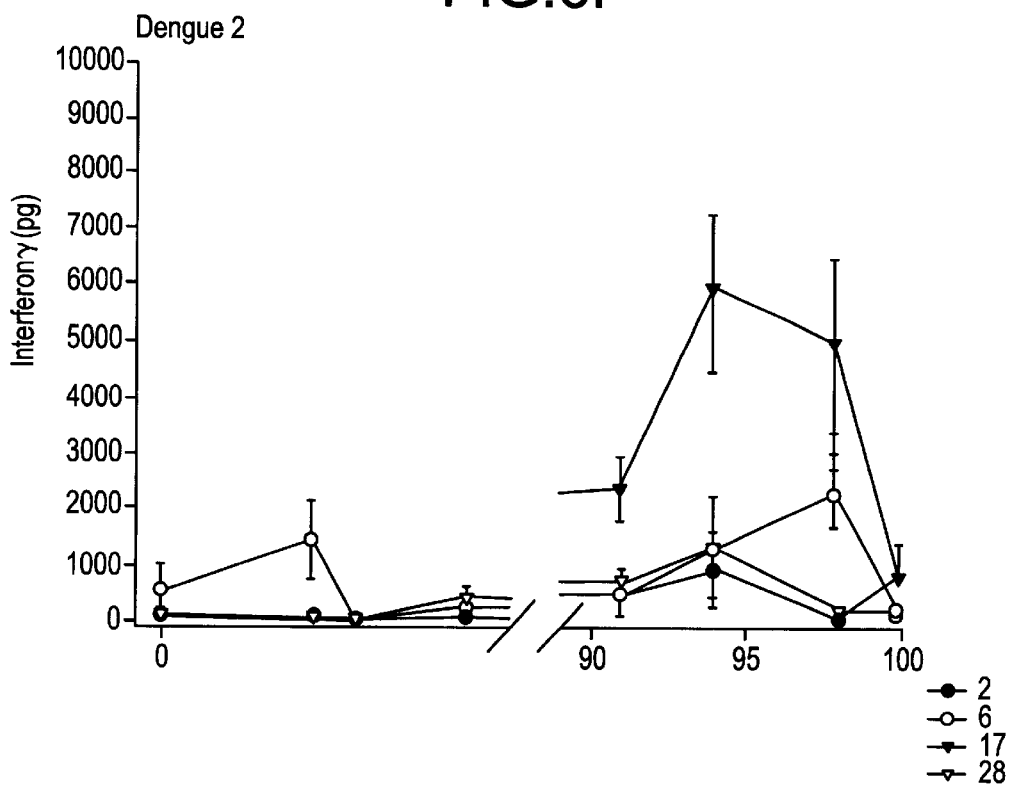
Figure 6G:
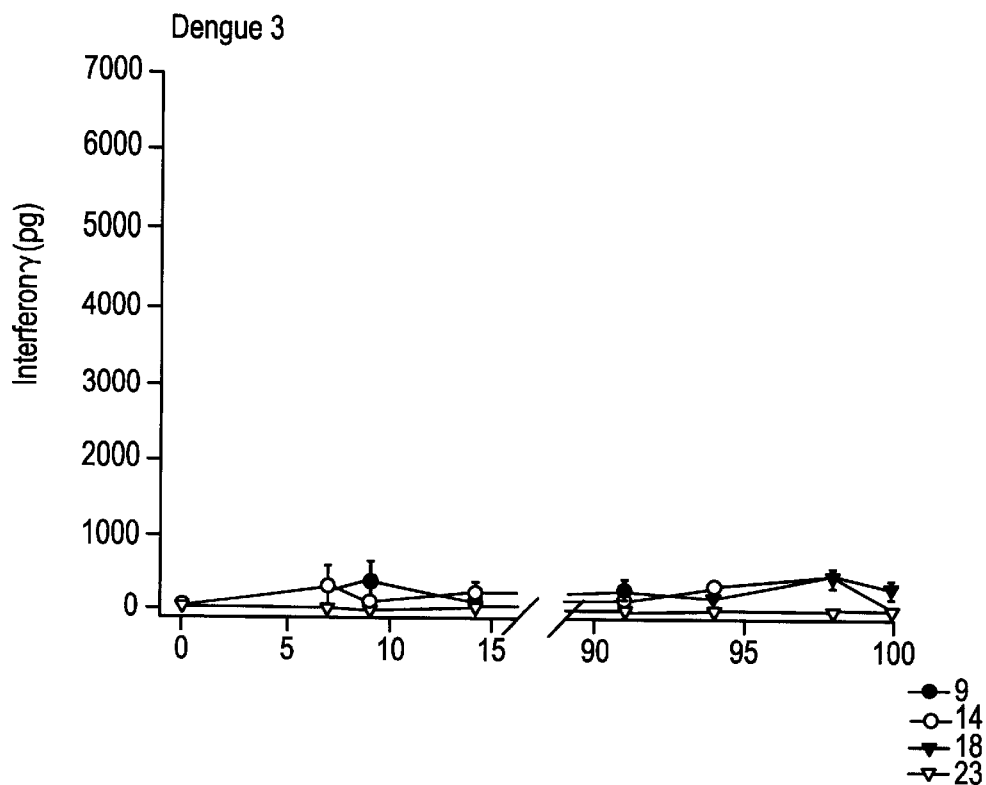
Figure 6H:
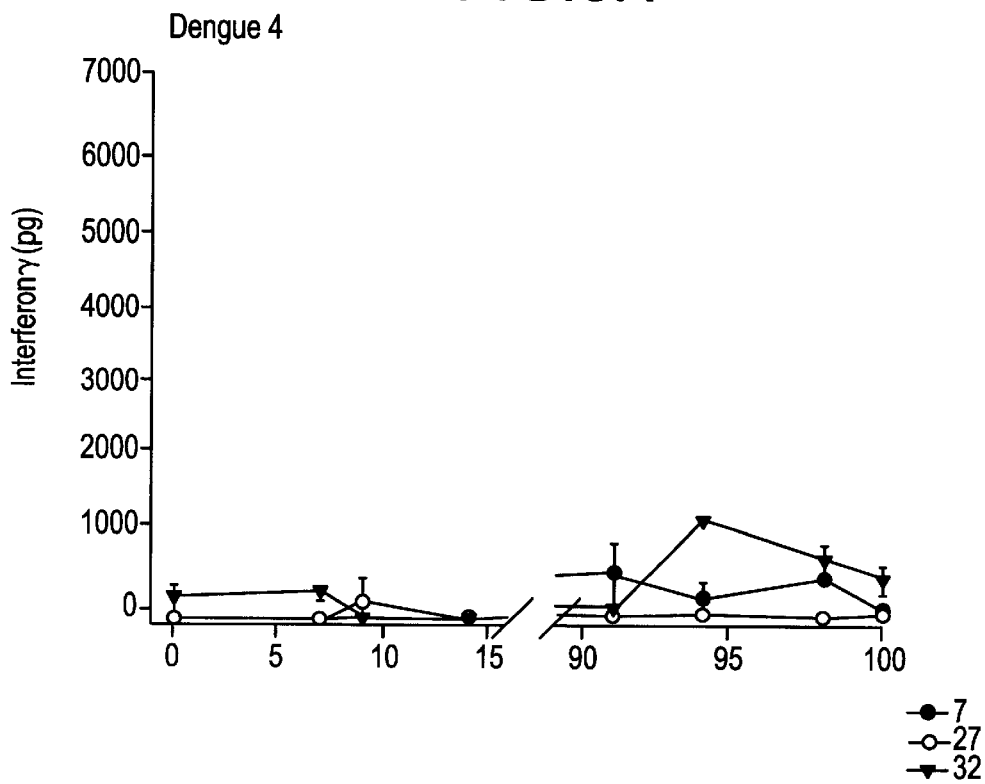
Figure 7A:
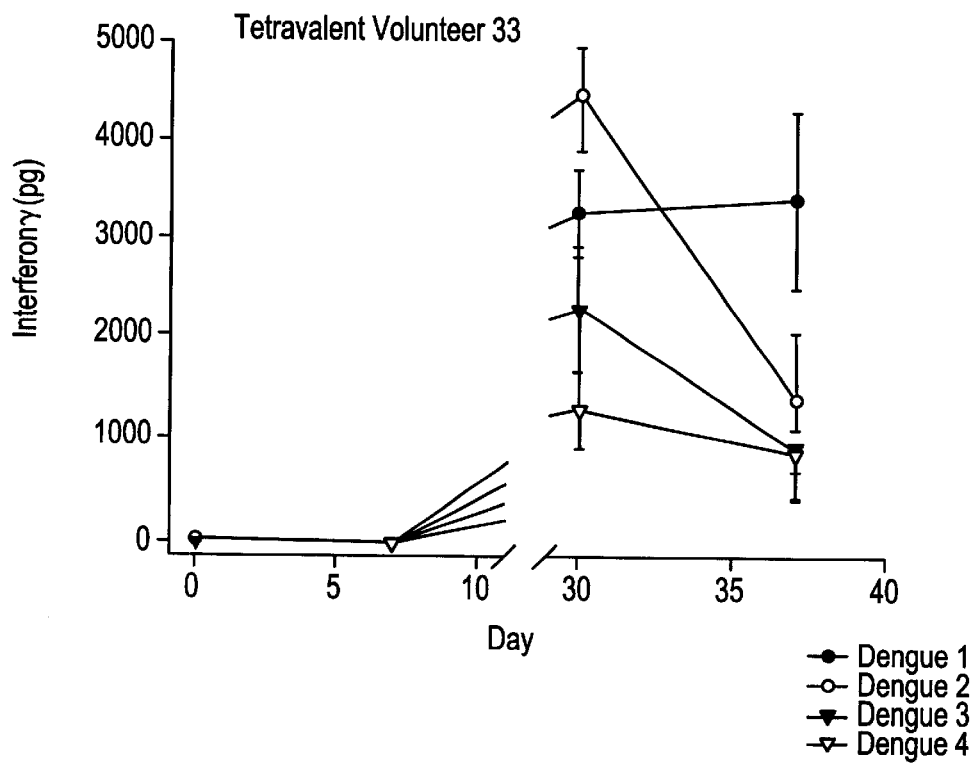
FIGS. 7A–D: Interferon γ production of PBMC collected from vaccine volunteers receiving tetravalent vaccine. The PBMC were stimulated individually with each serotype of virus. Individual lines in each graph represent responses of one volunteer's PBMC to individual serotypes of virus. As with the monovalent vaccine recipients, late responses were noted.
Figure 7B:
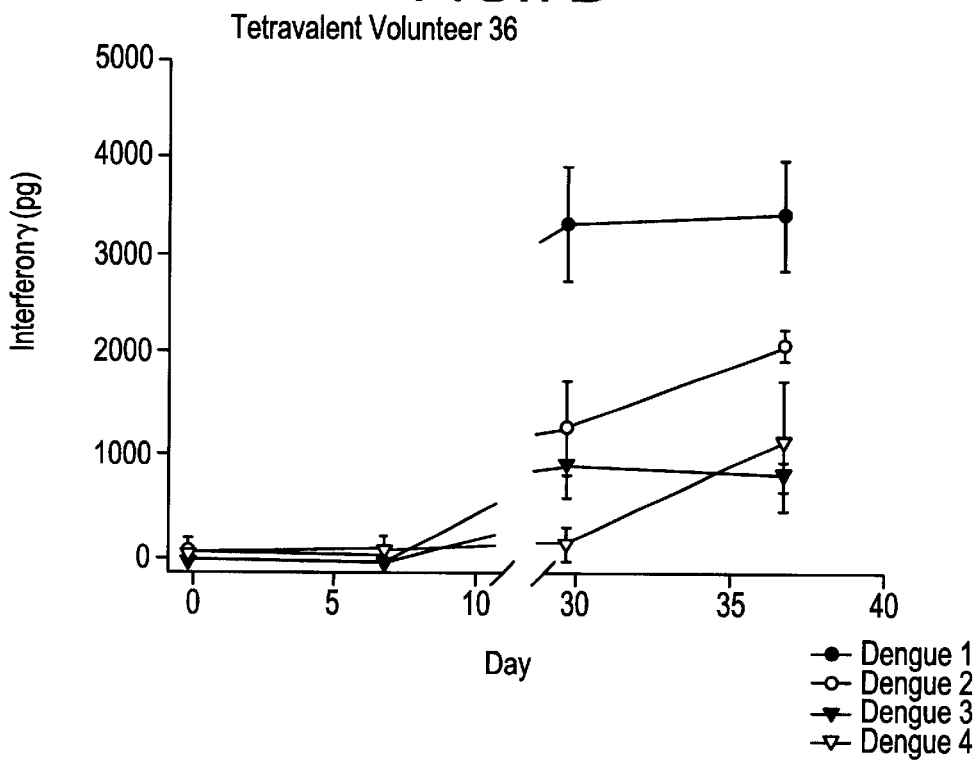
Figure 7C:
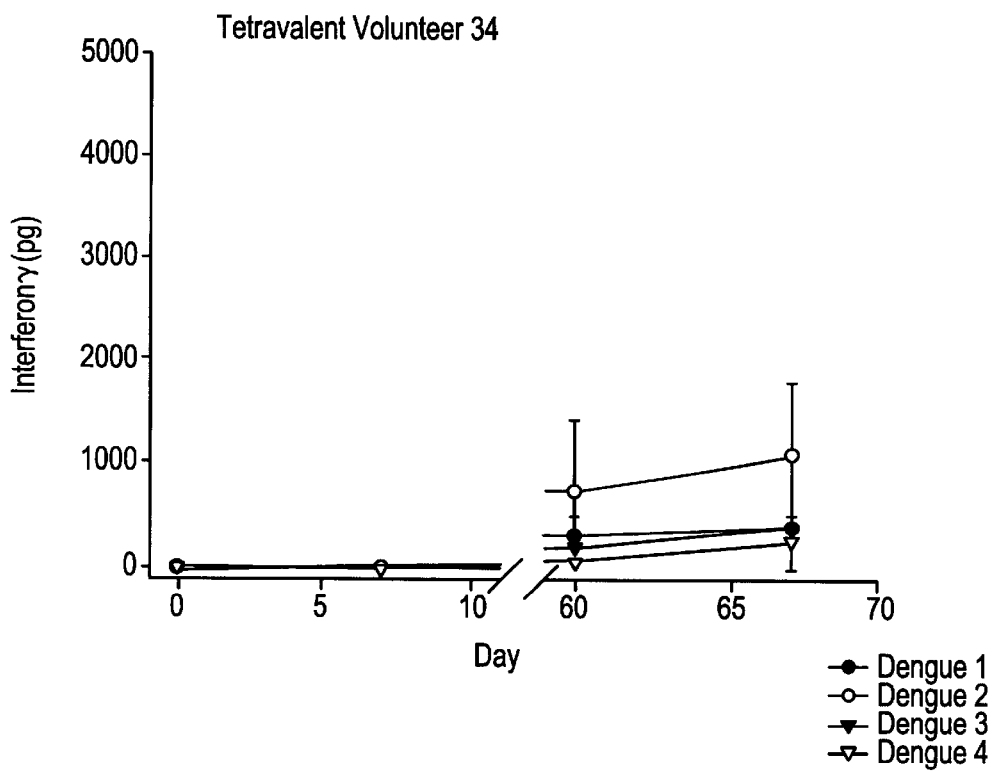
Figure 7D:
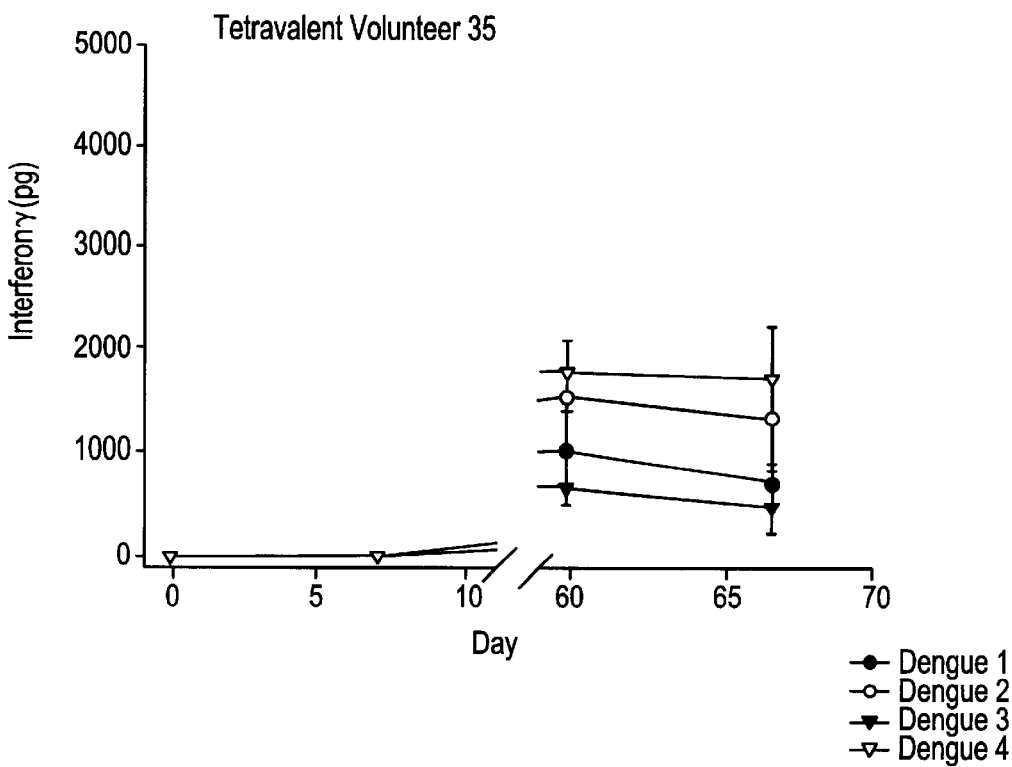

FIG. 2 shows the frequency distribution of RI by serotype. Eight subjects (14%) developed fever (>100.4° F.). Of the eight 4 received DEN-1, 1 DEN-2, 1 DEN-3 and 2 tetravalent. Highest and longest fever ocurred in a DEN-1 recipient with T$_{max}$ of 103.3° F. and fever of 3 days. Only one other subject, who also received DEN-1, had more than one day of fever. Seven of the eight episodes of fever occurred following the first vaccination.

Sixteen subjects(27%) developed a generalized rash, involving the trunk and extremities from their first vaccination. Rash was usually erythematous, macular papular and mildly pruritic. Only 7 of the 16 with generalized rash had fever. Of the 16 subjects with rash five received DEN-1, two DEN-2, one DEN-3, three DEN-4 and five tetravalent. Rash typically became noticeable by day 8–10 after vaccination and resolved in 3 ?4 days. No subjects developed any petechiae, purpura or scarring. No subjects developed rash from revaccination.

Gastrointestinal symptoms were relatively common, occurring in a third of subjects, but they were mild and brief, lasting less than 24 hours. One DEN-4 recipient developed severe nausea associated with crampy abdominal pain for one day.

Six subjects(10%), 5 dengue and 1 yellow fever 17D recipient, developed transient neutropenia with absolute neutrophil count less than 1000/ml. The lowest was 288 in a DEN-1 subject. Neutropenia typically resolves in 2-3 days. No subject developed thrombocytopenia. There were no clinically significant elevations in AST or ALT.

As expected of this group of non-immune adult receiving their first dengue virus exposure none developed any clinical evidence of dengue hemorrhagic fever.

EXAMPLE 8

IMMUNOGENICITY

Viremia was detected in 10 subjects (17%), one received DEN-2, four DEN-3, one DEN-4 and four tetravalent. No DEN-1 viremia was detected. The serotype(s) of the virus isolated from the tetravalent subjects have yet to be identified. All detected viremias occurred after the first dose of virus. Curiously fever ocurred with viremia only in 3 tetravalent recipients. All viremic subjects developed neutralizing antibody. One did not develop IgM or IgG response even with viremia.

Table 11 summarizes the antibody responses to monovalent vaccination. Neutralizing antibodies were detected more frequently than the IgM and IgG. No seroconversion was detected by IgM or IgG that was not also found by the $PRNT_{50}$ of 1:10 serum dilution. When present, IgM were positive in 41% by 14 days after vaccination, in 17% by 21 days and 42% by 30 days. IgM typically peaked by day 30 after first vaccination. A single exception was in a tetravalent recipient whose IgM peaked three days after his second vaccination. IgM can persist for more than 3 months. The seroconversion rates by neutralizing antibody were 100%, 92%, 54% and 58% for monovalent serotypes 1,2,3 and 4 respectively. When present, neutralizing antibody was typically detectable by day 30 after first vaccination. No time points between day 0 and 30 were assessed for neutralizing antibody. The second dose of vaccine boosted DEN-2 GMT by over four-fold, which was not seen with the other serotypes. Two DEN-3 subjects seroconverted after a second dose of vaccine, one at 1 month and the other at 3 months. They had not developed neutralizing antibody after one dose. Interestingly the IgM/IgG patterns of these two subjects suggest a secondary response after their second dose suggesting they were immunologically sensitized by the first dose.

Despite pre-entry negative hemagglutination inhibition assay for dengue, SLE, JE and YF 5 of 53 (9%) subjects tested developed a secondary antibody response pattern with IgM to IgG ratio of <1.8. All 5 were negative for homologous dengue neutralizing antibody prior to vaccination. This suggests a previous occult exposure to flavivirus. We found no significant difference between the mean RIs of secondary and primary antibody responders (9.6 vs 5.8, p=0.19).

There were 12 monovalent subjects who did not develop IgM/IgG or neutralizing antibody. One received DEN-2, six DEN-3 and five DEN-4. The mean reactogenicity index for this group of antibody non-responders was less than 1 which was significantly different from the mean RI of type 2,3 and 4 neutralizing antibody responders. (0.9 vs 4.9, p<0.003).

Our studies included 25 blacks and 31 Caucasian subjects. There was no significant difference between the mean RIs of these two racial groups. This is of interest because there is some epidemiologic evidence suggesting milder dengue disease severity among blacks.

TABLE 11

Monovalent vaccine seroconversion rates by IgM and $PRNT_{50}$

| Vaccine | Seroconversions after 1st by IgM(+) $PRNT_{50}$ | First Dose $GMT^{-1}$* | Seroconversions after 2nd by IgM(+) $PRNT_{50}$ | Second Dose $GMT^{-1}$* | Cumulative Seroconversions by IgM | $PRNT_{50}$ |
|---|---|---|---|---|---|---|
| DEN-1 | 10/12 12/12 (100%) | 668 | 0/2 — | 513 | 10/12 | 12/12 (100%) |
| DEN-2 | 9/12 11/12 (92%) | 112 | 0/3 0/1 | 559 | 9/12 | 11/12 (92%) |
| DEN-3 | 4/13 6/13 (53%) | 15 | 2/9 1/7 | 16 | 6/13 | 7/13 (54%) |
| DEN-4 | 5/12 7/12 (58%) | 17 | 0/7 0/5 | 9 | 5/12 | 7/12 (58%) |
| YF 17D | 0/4 4/4 (100%) | 2935 | — — | — | 0/4 | 4/4 (100%) |

*used 30-day post vaccination titer; used value of 1 for negative titer in calculation
— = not done

TABLE 12

Reactogenicity and Immunogenicity of Tetravalent Vaccine Recipients

| Volunteer | Vaccine Schedule (months) | Reactogenicity Index | | | Serotypes Neutralizing Ab Measured 30 days after | | |
|---|---|---|---|---|---|---|---|
| | | Dose 1 | Dose 2 | Dose 3 | Dose 1 | Dose 2 | Dose 3 |
| 33 | 0, 1 | 16 | 0 | — | 1, 2, 3, 4 | 1, 2, 3, 4 | — |
| 34 | 0, 1 | 0 | 0 | — | 2 | 1, 2 | — |
| 35 | 0, 1 | 4 | 0 | — | 1, 2, 3, 4 | 1, 2, 3, 4 | — |
| 36 | 0, 1 | 15 | 3 | — | 1 | 1, 3 | — |

TABLE 12-continued

Reactogenicity and Immunogenicity of Tetravalent Vaccine Recipients

| Volunteer | Vaccine Schedule (months) | Reactogenicity Index | | | Serotypes Neutralizing Ab Measured 30 days after | | |
|---|---|---|---|---|---|---|---|
| | | Dose 1 | Dose 2 | Dose 3 | Dose 1 | Dose 2 | Dose 3 |
| 37 | 0, 1, 4 | 2 | 0 | 0 | 1 | 1 | 1, 2, 3 |
| 38 | 0, 4 | 35 | 14 | — | 1, 2 | 1, 2, 3 | — |
| 39 | 0, 1, 4 | 18 | 0 | 0 | 1, 3, 4 | 1, 3 | 1, 2, 3, 4 |
| 40 | 0, 1, 4 | 2 | 0 | 0 | 1 | 1 | 1, 3 |
| 41 | 0, 1, 4 | 1 | 2 | 0 | 2 | 2 | 1, 2, 3, 4 |
| 42 | 0, 1 | 0 | 0 | — | 2 | 1, 2 | — |

TABLE 13

Seroconversion rates of Monovalents and Multiple Doses of Tetravalent

| Vaccine | DEN-1 Ab | DEN-2 Ab | DEN-3 Ab | DEN-4 Ab |
|---|---|---|---|---|
| Monovalent 1 dose | 12/12 | 11/12 | 6/13 | 7/12 |
| Tetravalent 1 dose | 7/10 $p < .05$ | 6/10 $p > .07$ | 3/10 $p > .4$ | 3/10 $> .18$ |
| Tetetravalent 2 doses | 9/10 | 6/10 | 5/10 | 2/10 |
| Tetetravalent 3 doses | 4/4 | 3/4 | 4/4 | 2/4 |

Age, Sex

Table 12 shows PRNT seroconversion results from the ten tetravalent vaccine subjects. The first 4 subjects received two vaccinations at 0 and 1 month. One subject missed his second vaccination on day 30 and was vaccinated on day 60. Six more subjects were to be vaccinated at 0 and 1 month and if response was incomplete a third vaccination at 4 month was administered. Two subjects developed neutralizing antibody to all 4 serotypes after a single dose. Another two tetravalent recipients seroconverted to all 4 serotypes after vaccination at 4 months. Two others developed trivalent responses. A second dose of the tetravalent given at 1 or 2 months did not significantly increase seroconversions. The overall seroconversion rates in these 10 tetravalent subjects were 100%, 80%, 80% and 40% for DEN-1,2,3 and 4 respectively.

EXAMPLE 9

A study was designed to evaluate interaction of each serotype component in tetravalent vaccine by a 2-level $2^4$ factorial design.

Fifty-four subjects were given 15 permutations of 2 dose levels of each serotype. Results are shown in FIG. 3. H, high dose, indicates undiluted vaccine, ranging between $10^5$–$10^6$ pfu/ml; L, low dose, indicates a 1:30 dilution of undiluted vaccine resulting in about $10^{3.5}$–$10^{4.5}$ pfu/ml.

Six subjects were given full-dose tetravalent vaccine at 0 and 1 month. If subject did not make tetravalent neutralizing antibody response, a third dose at 4 months was given. Results are shown in FIG. 4.

Four human subjects were given syringe-mixed full-dose tetravalent vaccine at time 0 and 1 month. Endpoints were clinical safety and neutralizing antibody at 1 month after second vaccination. T-cell responses were measured in the first 4 subjects. Results are shown in FIG. 5.

Results indicate that tetravalent vaccine (16 formulations) were found to be safe in 64 non-immune American volunteers. Reactogenicity varied. Four formulations elicited trivalent or tetravalent neutralizing antibody responses in all volunteers. In concordance with monovalent experience, a second dose of tetravalent vaccine at 1 month did not induce significant reactogenicity but also did not augment neutralizing antibody responses. End titration of neutralizing antibody responses is in progress. Memory interferon-gamma responses in T-cells can be measured in the absence of neutralizing antibody. Dosing intervals ≧4 months may result in improved tetravalent seroconversion.

Discussion

These vaccines appear attenuated in humans when compared with historical descriptions of experimental infections with wild-type dengue. (Simmons et al., 1931, Manila Bureau of Printing) We used a numeric scale based on self-reported symptom duration and severity to quantify reactogenicity. Such method tends to over estimate vaccine-related reactions. Ideally it should be validated with cases of natural dengue infection. However, imprecise the RI allowed us to reasonably compare symptoms between individuals and groups. Results from testing the monovalent vaccines showed the degree of attenuation to be variable among the four dengue vaccine candidates. 45AZ5 PDK20 is the least attenauted, highest titer and resulted in uniform seroconversion. The DEN-2 candidate, S16803 PDK50, similarly resulted in nearly 100% seroconversion with a benign reactogenicity profile. The Den-3 and Den-4 had low reactogenicity profiles but seroconversion rates were only 50–60%. It should be noted that the doses of type 3 and 4, the less immunogenic strains, are ten-fold less than that of types 1 and 2.

The second dose of virus was associated with remarkably little reactions. However, the benefit of a second dose of monovalent vaccine at 1 or 3 month is small. Den-1 and 2 were already near uniformly immunogenic such that an additional dose may be superfluous. Nevertheless the GMT of Den-2 was boosted over four-fold. This may be evidence of low level viral replication after the second dose or the dose contains sufficient antigenic mass to elicit a booster response. This pattern of neutralizing antibody response has also been seen with second vaccination with 17D YF. (Wisseman, 1962, Am J Trop Med Hyg 11, 570–575) The first dose of Den-3 may have sensitized the two monovalent subjects who seroconverted after the second dose with secondary antibody response pattern. This suggests that our neutralizing antibody assay may not be sensitive enough to detect the appropriate immune response to type 3 vaccine candidates. The second dose did not add any new seroconverters to type 4. There was no obvious additional benefit in giving a second dose of monovalent DEN-1 or DEN-4 with the dose and schedule tested.

Twelve monovalent subjects who did not make neutralizing antibody response to monovalent vaccines also did not respond with measurable dengue IgM or IgG. All these non-responders received viable virus from the same vial that clearly replicated in other subjects. They developed no reactions to the vaccinations. Thus, by all indications there was no evidence of virus replication in these subjects. The mechanism for this nonresponsiveness is unknown. It may be the result of lack of host substrate necessary for infection or an effective innate immunity.

The value of multiple dosing may be more apparent in combination live-attenuated vaccines as a strategy to circumvent viral interference. Here dose of each component as well as the dosing interval may be important. Interference and enhancement can potentially occur when dengue viruses are given in combination. Four subjects developed neutralizing antibody to all 4 serotypes, two after the first dose, and two after a third dose at 4 months. Four of five volunteers who received revaccination at 4 months seroconverted to 3 or more serotypes. The explanation of this difference may be that at one month after vaccination there is sufficient cross-reactive neutralizing antibodies to suppress replication of heterotypic viruses in the vaccine. Sabin found that there was such transient cross protection lasting up to 3 months when human subjects were given one serotype virus. (Sabin, 1959, Viral and Rickettsial Infections of Man. Philadelphia: JB Lippincott Company). Our future tetravalent studies will use a 0, 6 month vaccination schedule.

The poor immunogenicity of of DEN-3 and 4 may be that at $10^5$ pfu/ml Den-3 and Den-4 doses are at replicative disadvantage compared to DEN-1 and 2, both of which are at $10^6$ pfu in the tetravalent formulation. We are exploring alternative production strategies to increase titers of DEN-3 and DEN-4.

Without detecting viremia of all 4 viruses in the tetravalent responders one cannot be certain that the presence of neutralizing antibody necessarily imply replication of all 4 serotypes. Measured neutralizing antibodies may be cross reactive and of low avidity. This problem should be addressed by looking at long-term persistence of antibody against each serotype. A sensitive and serotype-specific RT-PCR assay would be useful to determine polyvalent viremia as evidence of viral replication.

Only two of the tetravalent vaccinees developed neutralizing antibody to all 4 serotypes after one vaccination. Such incomplete response to tetravalent vaccine raises questions about risk of dengue hemorrhagic fever in the setting of exposure to virulent heterologous serotypes. If antibody-dependent enhancement is the pathophysiologic mechanism for DHF risk may be present even when all four serotype antibodies are elicited by vaccination but one or more serotype antibody wanes differentially below neutralizing threshold. We report below that TH1 T-cell response can be measured in these tetravalent vaccinees even in the absence of neutralizing antibody. Would that be sufficient to protect? These questions may only be answered by careful long-term field testing of tetravalent vaccines in endemic areas.

In conclusion, our results indicate that the four serotypes are variably reactogenic as monovalent vaccines with type 1 more so than serotypes 2,3 and 4. Serotypes 1 and 2 elicited neutralizing antibody in >90% while serotypes 3 and 4 are less immunogenic. The tetravalent combination is safe, reasonably well-tolerated and induced neutralizing antibody to all 4 serotypes in four of ten subjects. Two doses of tetravalent vaccine did not improve seroconversion rates at the one or two-month dosing intervals tested. A longer dosing interval of over 4 months may improve seroconversion rate.

EXAMPLE 10

Material and Methods for T-cell Response to Denaue Vaccines

Subjects. Thirty-five healthy adult volunteers ages 18–50 (21 males, 14 females) participated in a phase I clinical trial, conducted by the Walter Reed Army Institute of Research, involving candidate dengue virus vaccines. The participants were selected from a group of volunteers based upon the absence of circulating anti-flavivirus antibody. Additional selection criteria was HIV negative status and good health based upon a physical exam and responses to a questionnaire.

Vaccine groups. Thirty individuals randomly received two doses of a live attenuated monovalent vaccine; four received two doses of a live attenuated tetravalent vaccine. One monovalent recipient (volunteer ID 1) quit the study after only receiving the first dose. Prior to vaccination, there was no detectable hemagglutination-inhibiting serum antibody to dengue virus types 1–4, Japanese encephalitis virus, St. Louis encephalitis virus, or yellow fever virus in any of the volunteers. Each dose was given as a 0.5 ml subcutaneous injection of undiluted virus(es).

PBMC collection. Peripheral blood (8 ml) was collected from each volunteer by venipuncture into Vacutainer Cell Preparation Tubes (CPT) [Becton-Dickinson, Franklin Lakes, N.J.] on day 0 and at five time points after the first dose but prior to the second dose(days 3, 7, 9, 14, 28/30/31/60 or 91). Blood was also collected on the day of the second dose and at four time points afterwards (days 3, 7, 9 and 14 post second dose). The time of administration of the second dose, depending on the volunteer, thus was approximately 1–3 months after the first dose. Variation in collection times around 1 month occurred due to variation in volunteer scheduling. Cells were separated from whole blood by centrifugation at 1000×g for 30 minutes. PBMC were collected (the cell layer above the gel in the CPT tube) and washed twice in Hank's balanced salt solution (Life Technologies, Rockville, Md.) with centrifugations at 500× g. Isolated PBMC were resuspended in 4 ml (per CPT tube) of Cell Freezing Media/DMSO (Sigma, St. Louis, Mo.) and frozen in 1 ml aliquots overnight at −70° C. The PBMC were then transferred to vapor phase liquid nitrogen for long term storage.

Vaccine viruses. The following live attenuated dengue virus strains described above were used in the monovalent vaccines: 45AZ5PDK20 (DEN 1), S16803PDK50 (DEN 2), CH53489 (DEN 3), 341750PDK20 (DEN 4). The tetravalent vaccine was an equal mixture of all four of these strains.

Cell culture viruses. The following dengue viruses, propagated in Vero cells, were used for PBMC stimulation in culture: Westpac 74 (DEN 1), S16803 (DEN 2), CH53489 (DEN 3), and TVP360 (DEN 4). All four serotypes were provided by Dr. Robert Putnak in 1 ml aliquots and stored at −70° C. until use. The virus titers ranged from 0.30–2.4× $10^6$ pfu/ml.

Bulk culture of PBMC and stimulation with live virus. Frozen vials of PBMC were removed from liquid nitrogen storage and gently thawed at 37° C. PBMC were washed twice with RPMI medium 1640 (Life Technologies, Rockville, Md.) and suspended in complete media containing 10% human male AB serum (Sigma) plus supplements [penicillin (100 U/ml)-streptomycin (0.1 mg/ml)-fungisone (0.25 mg/ml) [Sigma], 2 mM L-glutamine (Life Technologies), and 0.5 mM 2-mercaptoethanol (Sigma)]. The cells were suspended at a concentration of 2.5 million cells/ml. Some assays required 3.25 million cells/ml. The PBMC (100 ml) were added to individual wells of a 96-well V-bottom plate (Costar, Acton, Mass.). An equal volume of dengue virus 1, 2, 3, or 4 diluted in 10% complete media at a concentration of 3000 to 24000 pfu/100 ml was added to each well. Control wells received an equal volume of medium without virus. The cells were then cultured at 37° C. in 5% $CO_2$ for four days.

Immunoassay

A chemiluminescent immunoassay was done to determine the quantity of lymphokine secreted in tissue culture supernatant at the end of 4 days of culture. A 96 well immunoassay plate, Microlite 2 (Dynatech Laboratories, Inc., Chantilly, Va.) was coated overnight with 50 ul/well of 10 mg/ml unlabeled anti-lymphokine (IL-4, IL-10, or Interferon γ) antibody (Pharmingin San Diego, Calif.) in a 0.1 M potassium bicarbonate buffer. The plates were washed and 100 ul I-block buffer (Tropix, Bedford, Mass.) was added for one hour. Standards (Recombinant IL-4, IL-10 and Interferon γ, Pharmingen, San Diego, Calif.) were pre diluted in I-block beginning with a concentration of 10 ng/ml. Eight-three fold dilutions of the standard were made. Samples, controls and standards were diluted in an equal volume of I-block buffer. Aliquots of 50 ul were added to each assay plate. The samples incubated for 1 hour at room temperature. The plates were washed. Secondary biotinlyated antibody was diluted 1:1000 in I-block and 50 ul/well was added to the assay plates. The plates were washed and 50 ul/well of avidin-alkaline phosphatase (Avidix AP, Tropix, Bedford, Mass.) was added to the assay plates. The plates were incubated for one hour at room temperature. The washed plates were incubated twice for one minute with assay buffer (Tropix). The CDP-Star substrate (Tropix) was added to each well (100 ul/well). After 10 minutes the plates were read on a MD2250 luminometer (Dyatech, Chantilly, Va.). The first specimens were assayed using a modified protocol. Instead of a detector step using avidin-alkaline phosphatase, avidin-aequorin (Sealite Sciences, Atlanta, Ga.) was used. This material became unavailable during the study so the protocol was modified. Results using standard and control specimens were identical for the two assay formats.

Serotype cross-reactivity. To examine serotype specificity, PBMC collected on days 42, 45, or 105 from selected recipients of the monovalent attenuated vaccines (see results)-were stimulated for four days @250,000 cells/well with each serotype of virus in independent cultures. Culture supernatants were then analyzed using the chemiluminescent lymphokine ELISA.

T cell subset depletions. To examine the specific cellular source of lymphokine production, PBMC were depleted of CD3+ or CD8+ T lymphocytes prior to stimulation. Selected PBMC were washed twice with RPMI medium 1640 and suspended at 3.25 million cells/ml in 5% complete media (30% more PBMC were used as input to compensate for cell loss during the depletion procedure). For the negative depletion, cells (650,000 PBMC) were incubated with washed antibody coated magnetic beads. Two types of beads were used, M-450 anti CD3 and anti CD8 beads (Dynal, Oslo, Norway). The anti CD3 beads were used at a concentration of 5.2 million particles/tube giving an approximate 20:1 bead to target cell ratio. The anti-CD8 beads were used at a concentration of 4.0 million particles per tube giving an approximate 31:1 bead to target cell ratio.) DYNABEADS™ (Dynal) in 1.5 ml microcentrifuge tubes. The cells were incubated at 4° C. for 30 minutes with moderate agitation. Non-depleted PBMC were used as controls. Using an MPC-2 magnetic particle concentrator (Dynal) labeled cells were removed from the cell mixture. CD3+ and CD8+ negatively selected PBMC were transferred to fresh microcentrifuge tubes. To remove any residual unbound cells, the concentrated Dynabeads were washed once with 200 ul complete medium. After transfer, the final volume (400 ul) was divided equally into two wells of a 96-well V-bottom culture plate. Depleted and control PBMC culture supernatants were analyzed after four days using the chemiluminescent lymphbkine ELISA. In addition, the cultured PBMC were assayed for intracellular granzyme B mRNA (see below). CD4+ depletion was performed similarly but the separation was done after stimulation using M-450 CD4+ (28.6 ml/4.004 million particles, an approximate 31:1 bead to target cell ratio) dynabeads. CD4+ negatively selected PBMC were assayed only for intracellular granzyme B mRNA.

Flow cytometry. Depletion efficiency (measured as % depletion) was determined using FACS analysis after dual staining of a randomly selected, unstimulated PBMC population (both non-depleted control and CD3+ or CD8+ depleted sets). The cells were incubated with PE labeled anti-CD4+ or anti-CD8+ and FITC labeled anti-CD3+ antibodies (Becton-Dickinson) for 30 minutes at 4° C. Labeled PBMC were then washed three times with fluorescence buffer [PBS (Sigma), 0.05% Na Azide, 1% Fetal Bovine Serum (Summit Biotechnology, Boulder, Colo.) and preserved in fluorescence fixative [PBS, 1% Formalin, 0.05% Na Azide] prior to analysis. Depletion efficiency, using the CD4+ Dynabeads, was not measured.

Granzyme B assay. Non-depleted control PBMC and T cell subset depleted PBMC were assayed for intracellular granzyme B mRNA, after four days of stimulation with wild-type virus. A Reverse Transcriptase Polymerase Chain Reaction (RT-PCR) assay in a 96-well plate format was used.

The mRNA purification was done using the "Straight A's" mRNA Isolation System (Novagen, Madison, Wis.). After centrifugation and removal of PBMC culture supernatants for lymphokine ELISA analysis, pelleted PBMC were lysed using 200 ul/well of lysis buffer containing 10 mM dithiothreitol and then incubated with 200 mg/well of washed oligo dT magnetic beads for 30 minutes at room temperature. After thoroughly washing the beads with eight volumes of wash buffer using a MPC-96 (Dynal) magnetic particle concentrator to remove DNA, proteins, and cellular debris, mRNA was eluted at 70° C. for 20 minutes with 200 ul/well of $H_2O$. The eluate was transferred to a 1.5 ml microcentrifuge tube and a second round elution performed with an additional 200 ml/well of $H_2O$. The 400 ul of eluate was next precipitated using 50 ul of 3M sodium acetate (pH 5.2), 20 mg of glycogen (Novagen), and 300 ul of isopropanol. After a final wash with 70% cold ethanol, the mRNA pellet was suspended in 30 ul of $H_2O$.

RT-PCR steps were performed in 96-well plates. Oligonucleotide primers (22 bp), which correspond to exons of the human granzyme B (CTLA-1) and amplify a 120 bp region, were synthesized by Dr. Stuart Cohen at the Walter Reed Army Institute of Research. The primers had the following sequences: grb2a (sense) 5'AGC CGA CCC AGC AGT TTA TCC C (SEQ ID NO:1), grb2b (anti-sense) 5'C TCT GGT CCG CTT GGC CTT TCT (SEQ ID NO:2).

For each reverse transcriptase reaction, the total reaction volume was 40 ul and included the following: $MgCl_2$ (5 mM), 10×buffer II (10 mM Tris-HCL, 50 mM KCL, pH 8.3), dNTPs (1 mM each), and RNase inhibitor (40 Units) [Perkin Elmer, Norwalk, Conn.] AMV reverse transcriptase (10 Units) [Siekagaku], grb2b primer (3 pmoles), $sH_2O$, and 4 ml of mRNA template. RT incubation steps were done in a 9600 thermocycler (Perkin Elmer) with parameters set at 42° C. (90 minutes), 99° C. (5 minutes), 4° C. (indefinitely). For each PCR, the total reaction volume was 50 ul and included the following: $MgCl_2$ (2 mM), 10×buffer II (same as above), dNTPs (0.4 mM each), amplitaq gold (1.25 Units), grb2a and grb2b primers (1 pmole each), $sH_2O$, and 5 ul of cDNA template. PCR incubation steps were also done in a 9600 thermocycler with parameters set at 95° C. initial denaturation/enzyme activation (10 minutes), 30 cycles: [95° C. denaturing (30 seconds with a 10 second ramp)/60° C. annealing (30 seconds with a 30 second ramp)/72° C. extension (30 seconds with a 30 second ramp)], 72° C. final extension (7 minutes), 4° C. (indefinitely).

Using electrophoresis, final amplified PCR products (10 ul) were separated on ethidium bromide stained 2% agarose (SeaKem)/1×TAE (Tris-Acetate-EDTA) gels and analyzed using a digital camera (Scientific Imaging Systems, New Haven, Conn.).

It was reasoned that if a booster response to a booster dose of live vaccine could be demonstrated, a more attenuated live virus vaccine could be used. The booster response sought was both an antibody and a T cell response.

While T cell responses to dengue vaccines have been measured, fewer measurements of T cell responses have been made than antibody responses. Therefore, the T cell response to administration of live dengue vaccine is less well characterized. One goal of this study was to determine the nature of the T cell response to the vaccines in terms of T helper response, serotype specificity and cytotoxic potential.

The predominating T cell response to these vaccines was a Th1 response. This was determined by the secretion of interferon γ by peripheral blood mononuclear cells (PBMC) stimulated by live dengue virus in a four day culture. The interferon γ was secreted by CD3+CD8− T cells. The T cell response was dengue virus serotype specific with some cross-reactive response. An anamnestic response was noted in some of the individuals and not others.

Lymphokine Secretion by Dengue Stimulated Cells

Live dengue virus was used to stimulate PBMC cultures. The serotype of stimulating virus used in culture was the same as the serotype of the vaccine virus. After four days, the tissue culture supernatants were assayed for the presence of interferon γ, IL-4 and IL-10. In all cultures, IL-4 and IL-10 were consistently negative. Two assay controls were used to insure that the assay was working properly. First, the standard curve used recombinant lymphokine and second, a control sample was used to insure that the lymphokines could be detected in the presence of tissue culture supernatant.

In contrast to the negative expression of IL-4 and IL-10, high levels of interferon γ were detected in several of the culture supernatants. FIG. 6 shows the kinetics of interferon γ expression of cells collected from volunteers receiving monovalent vaccines. Overall, the highest interferon γ responses were by PBMC collected from recipients of dengue 1 and dengue 2 candidate vaccines, though there were a few high responses in dengue 3 and 4 recipients. The interferon γ was occasionally detected by the 14th day after the first inoculation but often the expression was not detected until just prior to or just after administration of the second dose. The kinetics of secretion was therefore much slower than expected. In regard to booster responses for the monovalent recipients in this study, there were no consistent patterns. Depending on the individual, interferon γ levels either increased or decreased after administration of the second dose.

Unstimulated PBMC from all volunteers at all collection points showed undetectable levels of interferon γ. The mean expression from stimulated day zero cells was 127 pg/ml with a standard deviation of 230 pg/ml.

For the monovalent vaccine recipients, there were 16 positive and 14 negative interferon γ responders (mean±3 standard deviations). Sixteen of thirty monovalent vaccine recipients had PBMC cultures with interferon g results >1000 pg/ml for at least one time point. Twelve had sustained interferon g secretion at >1000 pg/ml for two or more consecutive time points. Also, twelve of thirty had secretion >1000 pg/ml on the last time point assayed.

Four volunteers received tetravalent vaccines (an equal mixture of all four monovalent strains). FIG. 7 shows the interferon γ production by PBMC collected from these tetravalent recipients. The PBMC were stimulated in separate cultures using one of each of the four serotypes of dengue virus. The PBMC from volunteers #33 and #36 secreted significant amounts of interferon γ, >1000 pg/ml, for at least one time point after stimulation with each of the four of the serotypes. The PBMC from volunteer #35 secreted significant amounts of interferon γ in response to three of the four serotypes (not dengue 3). The PBMC from volunteer #34 secreted significant interferon-gamma only in response to dengue 2 virus. Highest responses were predominantly to DEN 1 and 2. The kinetics of interferon γ production was delayed in the tetravalent vaccine volunteers as it was in the monovalent volunteers. High levels of interferon γ were detected just prior to and after inoculation of the second dose. In regard to booster responses, as with the monovalent recipients, there were no consistent interferon secretion γ patterns after administration of the second dose.

In aggregate, these results indicate that the predominant T lymphocyte response in both monovalent and tetravalent vaccine recipients was an antigen specific Th1 response.

EXAMPLE 11

Serotype cross-reactivity. PBMC from twelve of the monovalent vaccine recipients were examined for the presence of dengue serotype-specific and cross-reactive responses. Based on kinetics, those individuals who secreted >1000 pg/ml of interferon γ in PBMC culture supernatants on the last time point (second to last collection day) were chosen. PBMC from the last collection day were stimulated in independent cultures for four days with each dengue serotype followed by analysis of secreted interferon γ in culture supernatants. Although there was some serotype cross-reactivity, the highest response was always seen in PBMC-stimulated with the same serotype virus as the original vaccination (Table 14). Thus the interferon γ responses seen in PBMC from these selected monovalent vaccine recipients were dengue serotype-specific.

Cross reactive responses were half (or less) of the serotype specific response. For Dengue 2 vaccine recipients, the highest cross-reactive response was with dengue 4 virus. For dengue 4 vaccine recipients, the highest cross-reactive response was with dengue 2 virus. For dengue 1 vaccine recipients, the cross-reactive responses varied. There was only one dengue 3 vaccine recipient in this group and that response was serotype specific.

TABLE 14

Serotype specific and cross-reactive interferon γ expression by PBMC collected from monovalent vaccine recipients. The PBMC collected from individuals receiving monovalent attenuated dengue vaccines were separately stimulated in culture with each of the four serotypes of dengue virus. A subgroup of cells was selected based upon an interferon γ production of at least 1000 pg/ml in other assays. Serotype specific responses were always the highest, however cross-reactive responses also were noted. Results are shown as supernatant interferon γ in picograms/ml.

| Volunteer | Serotype | Dengue 1 | Dengue 2 | Dengue 3 | Dengue 4 |
|---|---|---|---|---|---|
| 4 | 1 | 1030 | 202 | 419 | 129 |
| 10 | 1 | 648 | 58 | 42 | 73 |
| 15 | 1 | 163 | 0 | 15 | 0 |
| 16 | 1 | 1731 | 51 | 250 | 506 |
| 22 | 1 | 546 | 200 | 159 | 47 |
| 29 | 1 | 168 | 0 | 26 | 0 |
| 31 | 1 | 375 | 0 | 0 | 0 |
| 11 | 2 | 690 | 5175 | 960 | 2610 |
| 20 | 2 | 797 | 6101 | 850 | 962 |
| 3 | 3 | 0 | 0 | 714 | 0 |
| 12 | 4 | 1239 | 1987 | 1067 | 4410 |
| 13 | 4 | 445 | 1391 | 11 | 4818 |

EXAMPLE 12

T cell subset depletions. To verify that this was a Th1 response, the identity of the cells secreting the interferon γ was determined. This was done by depleting T cells or T cell subsets prior to culture. The cells used in this study were mixed PBMC separated from whole blood using density gradient centrifugation. The predominant cells in PBMC populations include T cells, B cells, monocytes and NK cells. For this assessment, we chose the time point of the highest interferon γ response based on kinetics in 13 monovalent and 3 tetravalent volunteers.

Cells were removed from PBMC using immunomagnetic cell separation. The depletion efficiency was assessed using flow cytometry in test depletions. Analysis of the cultured PBMC was not done because of the small number available. In the test depletions, removal of CD3+ cells using CD3 monoclonal antibody resulted in a 92% reduction of CD3+ cells relative to non-depleted PBMC controls. The CD3 depletion was monitored using dual labels for CD3 and CD4, dual labels for CD3 and CD8, and single label for CD3. The CD3 depletion was more thorough for CD4+ cells than CD8+ cells with 98% of the CD3/CD4 T cells being depleted and 90% of the CD3/CD8 cells being depleted in the CD3 depleted groups. Removal of CD8+ cells using CD8 monoclonal antibody resulted in a 99.9% reduction of CD8+ cells.

Selected PBMC were depleted of CD3+ or CD8+ T lymphocytes, stimulated in culture with dengue virus for four days, and then examined for secreted interferon γ. Results were compared to those obtained from non-depleted PBMC controls cultured at the same time. CD4+ T lymphocytes were not depleted prior to stimulation because other cell populations need CD4+ T help for production of interferon γ.

Removal of CD3+ cells prior to culture substantially reduced the production of interferon γ as shown in Table 15. The range for reduction in interferon γ after CD3+ depletion was 59–100%. Reduced but significant interferon γ production was seen in some CD3+ depleted cultures. This residual production indicates that either the small amount of residual CD3+ cells remaining after immunomagnetic cell separation are secreting interferon γ and/or another population of cells is also secreting interferon γ.

TABLE 15

Lymphocytes secreting (or inducing the secretion of) interferon γ are CD3+ CD8-T cells. Selected lymphocyte subsets were negatively depleted using immunomagnetic cell separation techniques. The remaining cells were stimulated with live dengue virus for four days and the culture supernatant was assayed for interferon γ. Depletion of CD3+ lymphocytes prior to culture negatively influenced the production of interferon γ.

| | Control | CD3 depleted | | CD8 depleted | |
|---|---|---|---|---|---|
| Volunteer | Interferon γ (pg/ml) | Interferon γ | % Change | Interferon γ | % Change |
| 3 | 883 | 0 | 100 | 565 | 36 |
| 4 | 3084 | 1038 | 66 | 5559 | [80] |
| 10 | 4295 | 1781 | 59 | 4271 | 0.6 |
| 11 | 525 | 88 | 83 | 633 | [21] |
| 12 | 10000 | 1017 | 90 | 10000 | 0 |
| 13 | 5977 | 385 | 94 | 8392 | [40] |
| 15 | 1365 | 255 | 81 | 1910 | [40] |
| 16 | 1861 | 84 | 95 | 2113 | [14] |
| 17 | 576 | 42 | 93 | 1265 | [120] |
| 20 | 4614 | 1329 | 71 | 4235 | 8 |
| 22 | 1303 | 39 | 89 | 1349 | [3.5] |
| 29 | 2478 | 5 | 99 | 5681 | [129] |
| 31 | 995 | 370 | 63 | 3057 | [207] |
| 33T | 2393 | 9 | 99 | 2114 | 12 |
| 35T | 10000 | 202 | 98 | 9637 | 4 |
| 36T | 3542 | 469 | 87 | 3257 | 8 |

Except in one individual, removal of CD8+ cells prior to culture did not reduce the production of interferon γ. In 9 of the 16 cultures, removal of CD8+ cells actually increased its production, possibly due to removal of suppression by these cells or by reducing the killing of infected antigen presenting cells by CD8+ cytotoxic lymphocytes.

Together, these results indicate that the interferon γ seen in these PBMC cultures is either secreted by CD4+ T lymphocytes and/or by cells influenced by CD4+ T lymphocytes. This supports the finding of a Th1 response.

EXAMPLE 13

Figures 8A, 8B:
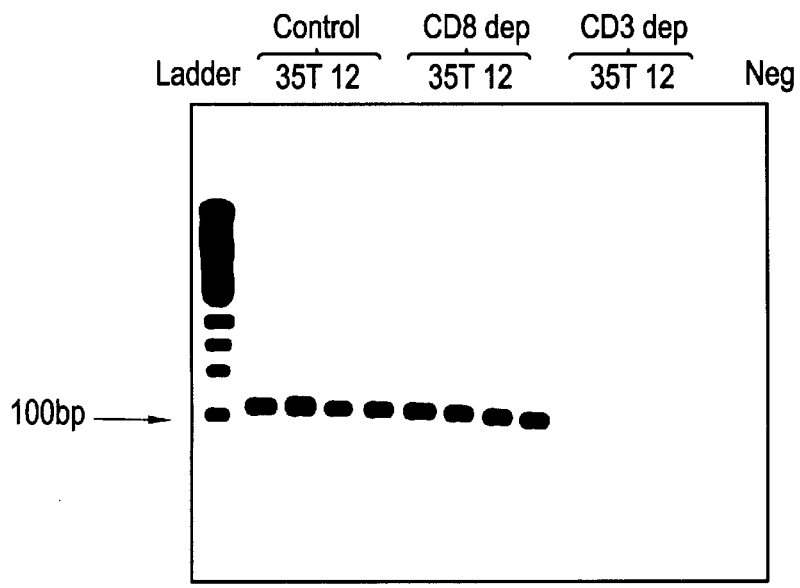
FIGS. 8A and B: Granzyme B mRNA production of PBMC collected from monovalent and tetravalent vaccine volunteers. Cells were collected from all individuals whose PBMC secreted $\geq$1000 pg IFNγ/ml at any time. This is a semiquantitative representation of the amount of mRNA detected by RTPCR. The upper chart (A) describes the intensity of bands seen for all samples. The lower gel (B) is from selected volunteers to show examples of positive and negative RTPCR assays.

Granzyme B. A Th1 response is associated with, among other things, a cytotoxic lymphocyte response. In an effort to see if cells capable of cell mediated killing were present in these vaccine volunteers, granzyme B mRNA was measured in the PBMC cultured for the depletion experiments. After removal of culture supernatants for lymphokine analysis, the cells were pelleted and lysed for extraction of mRNA. Granzyme B specific primers were used for RT-PCR. The PCR product was analyzed by agarose gel electrophoresis. Gel band intensity was converted into a +, − scale using a reference photograph (FIG. 8) for comparison. Extra cells from seven of the volunteers were cultured without virus. The unstimulated PBMC, from these seven volunteers, had little (− or +) granzyme B mRNA expression. With antigen-specific stimulation, expression was substantially upregulated in all 16 of the selected vaccine recipients (FIG. 8). T cell subset depletion using CD8 monoclonal antibody did not significantly reduce granzyme B expression relative to control PBMC. There were 3 individuals (ID 16, 22, and 33) whose granzyme B expression was reduced in the CD8 depleted group. In one (ID 33), the decrease was substantial. In contrast, T cell subset depletion using CD3 monoclonal antibody reduced expression in 14 of the volunteers. In 8 of the monovalent volunteers and in all 3 tetravalent volunteers, the decrease was substantial. Four of the interferon γ non-responders were also examined for granzyme B mRNA. All showed low levels of expression (data not shown).

In cells from seven of the volunteers, T cell subset depletion using CD4 monoclonal antibody was done after the four days of culture. The depletion was done after culture in order to provide T helper activity to all cells needing help during culture. Removal of CD4+ cells after stimulation did not affect granzyme B expression relative to non-depleted controls in the seven volunteers analyzed. Thus, although there is an antigen dependent production of granzyme B mediated by CD4+ Th1 cells, the actual cells that produce the granzyme B appear to be cells other than T cells. Whether this is production by NK cells or macrophages is unknown.

Discussion

Two objectives of this study were to determine if there was a measurable T cell response in the vaccine recipients and if a cell mediated response to the second dose of vaccine could be seen. For those objectives, T cell response kinetics were measured by re-stimulating cells collected at intervals around the two doses. The re-stimulation was done with live virus in bulk cultures of PBMC collected during the study.

A third objective of this study was to determine the nature of the T cell response in terms of 1. cell type defined by lymphokine repertoire, 2. dengue serotype specific and cross-reactive responses, and 3. a measure of cytotoxic potential, granzyme B production. These responses were measured in PBMC from both monovalent and tetravalent vaccine recipients. In regard to the tetravalent vaccine recipients, it was important to determine if a response could be detected to all four serotypes of dengue virus.

Human and mouse T helper responses can be divided into two groups based upon their pattern of lymphokine expression 5. T helper 1 (Th1) cells are characterized by the secretion of IL-2 and interferon γ. Of those two lymphokines, interferon γ is the most important in terms of identifying Th1 cells. T helper 2 (Th2) cells are characterized by the secretion of IL-4, IL-5, IL-6 and IL-10. In mixed populations of cells or PBMC bulk culture, one of the two secretion patterns usually predominates.

One factor influencing the Th1 vs Th2 response is the nature of the assaulting infection. Viral infections, and some bacterial infections such as Listeria and Mycobacterium (Peters, 1996, *Hepatology* 23, 909–916) often induce a Th1 response while some parasitic infections will induce a Th2 response (Conrad et al., 1990, *J Exp Med* 171, 1497–1508). The proportion of the two responses may vary during the course of the infection. For instance, even though viral infections usually begin with a Th1 response, a Th2 response can be produced later in the infection. The initial Th1 response may augment CTL responses and direct immunoglobulin isotype switching while the following Th2 response may augment antibody production by B cells.

In natural dengue infection, one study showed a Th1 response in most individuals. The Th1 response was associated with an effective immune response without associated severe pathogenesis. In contrast, some individuals developed a Th2 response that was associated with greater pathogenesis.

In spite of the association of a Th1 response with an effective anti-dengue immune response, the key lymphokine of a Th1 response, interferon γ, has both positive and negative influences on the immune response. In Thailand, Kurane found high levels of interferon γ in the serum of DHF patients in comparison to lower levels in the serum of DF patients (Kurane et al., 1991, *J Clin Invest* 88, 1473–1480). The increased interferon γ may be a measure of immune activation. Interferon γ is needed to activate and maintain activation of cytotoxic cells (CD4+ T cells, CD8+ T cells and NK cells). While this mechanism may contribute to pathogenesis in severe infections, the same response may be beneficial in milder infections by reducing the number of virally infected cells through antigen specific cytolysis. The positive; role of interferon γ in controlling dengue virus infection is demonstrated in a recent mouse knockout model deficient in interferons α, β and γ. The knock-out mice were susceptible to lethal infection by dengue viruses in contrast to normal adult controls that were resistant to infection (Johnson and Roehrig, 1999, *J Virol* 73, 783–786).

Alternatively, interferon γ may contribute to the pathogenesis of dengue virus infection. One mechanism for the pathogenesis may be by immune enhancement due to increasing the infection of one major target cell, the macrophage. In culture, interferon γ increased the antibody-mediated infection of a macrophage cell line U937 by increasing the number of Fc receptors on the surface of the cells (Kontny et al., 1988, *J Virol* 62, 3928–3933). Although another study using normal cultured macrophages showed the opposite effect of decreasing the infection (Sittisombut et al., 1995, *J Med Virol* 45, 43–49). Given these conflicting results, it is unclear whether interferon γ contributes to increased infection of macrophages.

In this study, a Th1 response was the predominant response. Assays for IL-4 and IL-10 were consistently negative indicating a lack of TH2 response. High levels of interferon γ were detected in the supernatants of many of the cultures, indicating the presence of a Th1 response in those cultures.

Since the stimulated cells were whole PBMC, the cells responsible for secretion of the interferon γ needed to be determined. This was done by depleting T cell subsets using an immunomagnetic procedure. Negative depletion was done prior to culture with antibodies recognizing either CD3 or CD8. Since CD3 depletion resulted in abrogation of interferon γ secretion and CD8 depletion did not, it was concluded that CD3+CD8− lymphocytes were the cell population secreting the interferon γ or at least controlling the secretion of interferon γ. This confirms that the interferon γ was the result of a Th1 response. Residual interferon γ in some cultures after depletion may have been due to some remaining CD4+ T lymphocytes after depletion or other cells in the culture, possibly Natural Killer cells or macrophages.

The peak interferon γ response was serotype specific. When cells from monovalent vaccine recipients were stimulated separately by each of the four serotypes of dengue viruses, the peak interferon γ production was in response to stimulation by dengue virus homologous to the vaccine virus. Lesser, cross-reactive responses to other dengue viruses were noted in several of the cultures. This is similar to the results obtained by others using a different measurement, lymphocyte proliferation. In one study, cells from individuals receiving a dengue 2 vaccine exhibited the greatest response to dengue 2 virus but cross-reactive responses were noted (Dharakul, *J Infect Dis* 170, 27–33). This was confirmed at the clonal level where the majority of clones obtained from a dengue 3 vaccine recipient responded best to dengue 3 antigen but had cross reactive responses to the other three dengue antigens (Kurane et al., 1989, *J Exp Med* 170, 763–775). The conclusion of the latter study was that primary dengue virus infection produces predominantly cross-reactive CD4+ lymphocyte responses (proliferation and interferon γ production).

In this study, cross-reactive responses of monovalent vaccine recipients' PBMC were usually half or less of the serotype specific response. In the tetravalent vaccine recipients, interferon γ secretion in response to individual serotypes of dengue virus was significant in three out of four tetravalent vaccine recipients. The responses varied within individual vaccine recipients enough that it was not possible to determine if the lower responses were serotype specific responses or cross-reactive responses.

The kinetics of T cell activation as indicated by interferon γ secretion was slower than expected. In a few instances, responses could be detected by day 14. However in most cases, responses were not detected until just prior to administration of the second vaccine dose. It is unclear what the reason is for the delayed kinetics. One explanation could be that antigen production by vaccine virus infected cells is slow and persistent. However, it is equally possible that the methods preferentially detected memory responses rather than acute responses. For instance, if active CD8+ cells were inhibiting a CD4+ response in PBMC collected during early infection, a measurable response may be attenuated. In cultures where the CD8+ lymphocytes were depleted, interferon γ secretion by the remaining lymphocytes was increased in more than half of the cultures. This inhibition may have been greater during early infection.

Others have observed more acute lymphokine production kinetics. Serum lymphokines, including serum interferon γ were measured for 17 days after inoculation with an attenuated dengue vaccine. An acute response was noted in that study that peaked during the time of viremia (Kurane et al., 1995, *J Clin Lab Immunol* 46, 35–40).

The response to the second dose was mixed. Some individuals showed an increase in interferon γ production while others showed a decrease. The interferon γ production by cells collected from vaccine recipients just prior to the second dose was high enough that it may have masked any anamnestic response to the second dose. In addition, the late interferon γ response may have made the measurement of an anamnestic T cell response more difficult. It is clear that some individuals responded to the second dose. This may indicate that there is some localized virus growth in the presence of an active immune response.

In summary, the predominant T cell response to administration of these live attenuated dengue viruses was a Th1 response. This was demonstrated by the secretion of interferon γ by re-stimulated PBMC collected from vaccine recipients. None of the PBMC cultures from vaccine recipient's cells had significant IL-4 or IL-10 secretion into the culture supernatant after re-stimulation. The Th1 response was verified by showing that CD3+CD8− lymphocytes were secreting the interferon γ. The Th1 response was predominantly dengue serotype specific but smaller cross-reactive responses were noted.

EXAMPLE 14

Clinical and Immunological Evaluations of Four Dengue Viruses as Challenge Strains in Immune and Susceptible Volunteers The primary objective of this study is to characterize clinical responses to each of 4 candidate dengue challenge viruses in susceptible and immune volunteers to judge their suitability as challenge strains for human vaccine efficacy studies. The secondary objective of the study is to generate hypotheses regarding the immune correlates of protection for dengue fever.

Dose, Schedule and Route: All volunteers will receive either 1 of 4 dengue challenge viruses or placebo in a single dose of 0.5 ml subcutaneously in the deltoid region on study day 0.

Study Groups:
Volunteer Set #1 (susceptible): to receive either DEN-1, DEN-2, DEN-3, DEN-4 or placebo Volunteer Set #2 (immune): to receive either DEN virus (serotype corresponding to previously received vaccine) or placebo General Eligibility Criteria: Age 18–35, excellent health without any chronic medical conditions, score of >75% on written study-comprehension examination, informed consent, availability for the study period, letter of approval for participation from chain of command (military only), serologic conversion in response to previous dengue vaccination (volunteer set #2 only)

Statistics: Data analysis will be primarily descriptive in this pilot study given the small number of volunteers in each test article group. The primary concern will be to document the frequency of clinical events (pre-specified and unexpected) within the four study groups as compared to placebo.

Pre-challenge immune measures and post-challenge immune responses of all challenged volunteers who develop dengue fever will be compared to those of all challenged volunteers who remain well, to develop hypotheses about immune correlates of protection.

Application of the Human Dengue Challenge Model: In contrast to most historical human dengue challenge experiments which were designed either to characterize dengue illness or to evaluate the attenuation of live vaccine candidates, this challenge study will aim to 1) validate 4 dengue viruses as challenge strains in flavivirus-naive volunteers (volunteer set #1), and 2) a identify correlates of immunity in recipients of monotypic dengue vaccine when subsequently challenged with homotypic dengue virus (volunteer set #2).

If the clinical-response in volunteer set #1 suggests these strains are suitable for challenge, then in future controlled experiments, these challenge strains will be administered to recipients of dengue vaccine candidates or placebo to select the most promising vaccine candidates for further development.

If the immunological response in volunteer set #2 suggests that some aspect of pre-challenge immunity (antibodies and/or T cell memory) correlate with protection, such correlates of protection could simplify dengue vaccine development.

Defining Criteria for Dengue Viruses to be Tested as Challenge Strains: A suitable dengue challenge virus will 1) reproducibly cause uncomplicated dengue fever lasting 3–7 days in volunteer set #1, 2) be produced in compliance with Good Manufacturing Practices (GMP) and be free of adventitious agents or reactogenic non-viral components, and 3) be available as lyophilized virus in sufficient quantity (>100 doses). Challenge Viruses include DEN-1 45AZ5 (PDK-0) inactivated, DEN-2 S16803 (PDK-10), DEN-3 cl 24/28 (PDK-0), DEN-4 341750 (PDK-6) (PDK=primary dog kidney cells).

Dose of each challenge virus in plaque forming units (pfu.) will be 0.5×titer.

The study challenge viruses meet the latter two criteria. This study aims to demonstrate that the study candidate challenge strains meet the first criterion. We have some evidence that the 4 challenge viruses to be tested in this study are appropriately pathogenic. The DEN-1 and DEN-3 challenge viruses have already been shown to cause uncomplicated febrile illness in volunteers. Though the DEN-2 and DEN-4 challenge viruses to be administered in this study are untested in volunteers, they are believed to be pathogenic, as they are the precursors of dengue virus vaccine candidates that were rejected because they caused febrile illnesses in volunteers. The only reason for rejecting any of the 4 study candidate dengue challenge viruses is if they cause either no illness in flavivirus-naive volunteers (volunteer set #1) or excessive illness in any volunteer (volunteer sets #1 and #2).

Volunteer Set #1: Ten healthy flavivirus-naive volunteers will be randomized to receive dengue virus challenge with 1 of 4 serotypes (2 volunteers per serotype) or placebo. The volunteers and investigators will remain blinded to the inoculum. We expect that the 8 volunteers who receive dengue challenge viruses will become moderately ill with 3–7 days of fever, severe headache and myalgias. Full recovery may take as long as 14 days from onset of illness. Each challenge virus will be deemed suitable based on the clinical responses of the 2 recipients and must satisfy the study definition of dengue fever. Dengue fever is defined as: an illness with: 2 or more of the following: headache, myalgia, erythematous rash, retro-orbital pain, arthralgias, and sustained fever for 48 hours or more allowing for periods of decreased temperature due to acetaminophen use, and tissue response during period of fever and days thereafter manifest by neutropenia or thrombocytopenia or liver injury, and evidence of dengue viremia during the period of fever.

Volunteer Set #2: Up to twelve young, healthy immune volunteers will receive homotypid dengue challenge virus (N=10, regardless of serotype) or placebo (N=2). Immune volunteers are previous recipients of monovalent, live-attenuated dengue vaccines who had a primary neutralizing antibody response. Immune volunteers are expected to remain well. Measures of their pre-challenge immune status or immune activation intra-challenge may identify correlates of protection.

SEQUENCE LISTING

5'AGC CGA CCC AGC AGT TTA TCC C (SEQ ID NO:1), grb2b (anti-sense) 5'C TCT GGT CCG CTT GGC CTT TCT (SEQ ID NO:2).

What is claimed is:

1. An immunogenic composition comprising two or more attenuated dengue viruses selected from the group consisting of a dengue-1 (DEN-1) virus having the sequence of DEN-1 strain 45AZ5 PDK-20 having the ATCC accession number VR-2648, a dengue-2 (DEN-2) virus having the sequence of DEN-2 strain S16803 PDK-50 having the ATCC accession number VR-2653, a dengue-3 (DEN-3) virus having the sequence of DEN-3 strain CH53489 PDK-20 having the ATCC accession number VR-2647, and a dengue-4 (DEN-4) virus having the sequence of DEN-4 strain 341750 PDK-20 having the ATCC accession number VR-2652, and a physiologically acceptable vehicle.

2. The immunogenic composition according to claim 1 which further comprises an adjuvant to enhance the immune response.

3. The immunogenic composition of claim 1, formulated in a dose of $10^2$ to $10^6$ PFU of attenuated virus.

4. A multivalent live attenuated dengue virus vaccine comprising any combination of dengue virus serotypes selected from the group consisting of: a dengue-1 (DEN-1) virus having the sequence of DEN-1 strain 45AZ5 PDK-20 having the ATCC accession number VR-2648, a dengue-2 (DEN-2) virus having the sequence of DEN-2 strain S 16803 PDK-50 having the ATCC accession number VR-2653, a dengue-3 (DEN-3) virus having the sequence of DEN-3 strain CH53489 PDK-20 having the ATCC accession number VR-2647, and a dengue-4 (DEN-4) virus having the sequence of DEN-4 strain 341750 PDK-20 having the ATCC accession number VR-2652.

5. The dengue virus vaccine of claim 4 wherein said dengue virus is produced in vertebrate cells.

6. The dengue virus vaccine of claim 5 wherein said cells are Vero cells.

7. The dengue virus vaccine of claim 4 wherein said dengue-1 virus is in the amount of $10^2$ to $10^7$ pfu/ml, said dengue-2 virus is in the amount of $10^2$ to $10^7$ pfu, said dengue-3 virus is in the amount of $10^2$ to $10^7$ pfu, and said dengue-4 virus is in the amount of $10^2$ to $10^7$ pfu/ml.

8. The dengue virus vaccine of claim 7 wherein said vaccine is administered subcutaneously.

9. An immunogenic composition comprising two or more attenuated dengue virus chosen from the group consisting of a dengue-1 (DEN-1) virus having the sequence of DEN-1 sawn 45AZ5 PDK-27 having the ATCC accession number PTA4810, a dengue-2 (DEN-2) virus having the sequence of DEN-2 strain S16803 PDK-S0 having the ATCC accession number VR-2653, a dengue-3 (DEN-3) virus having the sequence of DEN-3 strain CH153489 PDK-20 having the ATCC accession number VR-2647, and a dengue-4 (DEN4) virus having the sequence of DEN-4 strain 341750 PDK6 having the ATCC accession number PTA4811, and a physiologically acceptable vehicle.

10. A multivalent live attenuated dengue virus vaccine comprising any combination of dengue virus serotypes selected from the group consisting of: a dengue-1 (DEN-1) virus having the sequence of DEN-1 strain 45AZ5 PDK-27 having the ATCC accession number PTA4810, a dengue-2 (DEN-2) virus having the sequence of DEN-2 strain S16803 PDK-50 having the ATCC accession number VR-2653, a dengue-3 (DEN-3) virus having the sequence of DEN-3 strain CH53489 PDK-20 having the ATCC accession number VR-2647, and a dengue-4 (DEN-4) virus having the sequence of DEN-4 stain 341750 PDK-6 having the ATCC accession number PTA-4811.

11. The vaccine of claim 10 wherein at least one virus os DEN-1 strain 45Az5 PDK-27 having the ATCC accessior number PTA-4810.

12. The vaccine of claim 10 wherein at least one virus is DEN-4 strain 341750 PDK-6 having the ATCC accessior number PTA-4811.

* * * * *